United States Patent
Moir et al.

(10) Patent No.: US 9,340,551 B2
(45) Date of Patent: May 17, 2016

(54) INHIBITORS OF BACTERIAL TYPE III SECRETION SYSTEM

(75) Inventors: Donald T. Moir, Concord, MA (US); Daniel Aiello, Worcester, MA (US); Norton P. Peet, North Andover, MA (US); John D. Williams, Watertown, MA (US); Matthew Torhan, Ayer, MA (US)

(73) Assignee: MICROBIOTIX, INC., Worcester, MA (US)

(*) Notice: Subject to any disclaimer, the term of this patent is extended or adjusted under 35 U.S.C. 154(b) by 0 days.

(21) Appl. No.: 14/232,445

(22) PCT Filed: Jul. 13, 2012

(86) PCT No.: PCT/US2012/046676
§ 371 (c)(1),
(2), (4) Date: Jan. 13, 2014

(87) PCT Pub. No.: WO2013/010082
PCT Pub. Date: Jan. 17, 2013

(65) Prior Publication Data
US 2014/0142134 A1    May 22, 2014

Related U.S. Application Data

(60) Provisional application No. 61/507,259, filed on Jul. 13, 2011.

(51) Int. Cl.
| | |
|---|---|
| *C07D 405/00* | (2006.01) |
| *A61K 31/44* | (2006.01) |
| *C07D 491/056* | (2006.01) |
| *A61K 31/443* | (2006.01) |
| *A61K 31/381* | (2006.01) |
| *A61K 31/53* | (2006.01) |
| *A61K 31/165* | (2006.01) |
| *A61K 31/36* | (2006.01) |
| *A61K 31/4355* | (2006.01) |
| *A61K 45/06* | (2006.01) |
| *C07C 235/34* | (2006.01) |
| *C07D 317/50* | (2006.01) |
| *C07D 405/12* | (2006.01) |

(52) U.S. Cl.
CPC .......... *C07D 491/056* (2013.01); *A61K 31/165* (2013.01); *A61K 31/36* (2013.01); *A61K 31/381* (2013.01); *A61K 31/4355* (2013.01); *A61K 31/443* (2013.01); *A61K 31/53* (2013.01); *A61K 45/06* (2013.01); *C07C 235/34* (2013.01); *C07D 317/50* (2013.01); *C07D 405/12* (2013.01)

(58) Field of Classification Search
None
See application file for complete search history.

(56) References Cited

U.S. PATENT DOCUMENTS

| | | | |
|---|---|---|---|
| 5,037,991 | A | 8/1991 | Henrick |
| 2005/0143373 | A1 | 6/2005 | Alanine et al. |
| 2005/0282824 | A1 | 12/2005 | Li |
| 2010/0120714 | A1 | 5/2010 | Finkelstein et al. |

FOREIGN PATENT DOCUMENTS

| | | |
|---|---|---|
| WO | WO 2008/127275 | 10/2008 |
| WO | WO 2010/118046 | 10/2010 |
| WO | WO 2010114636 A1 * | 10/2010 |

OTHER PUBLICATIONS

CAPLUS 1983:453389.*
Silverman, R. "The Organic Chemistry of Drug Design and Drug Action," 2004, Elsevier, pp. 29-32.*
Meanwell, N. J. Med. Chem. 2011, vol. 54, pp. 2529-2591.*
Aiello et al., "Discovery and Characterization of Inhibitors of Pseudomonas aeruginosa Type III Secretion", Antimicrob. Agents Chemother., 54(5): 1988-1999 (2010).
Aiello et al., "A Novel Stereo-Specific Inhibitor of P. aeruginosa Type-Three Secretion", Abstracts of the Interscience conference on Antimicrobial Agents and Chemotherapy, 49: 183 (2009).
Babichev et al., "2-(2'—Benzothiazolylmethyl)- and 2-(2'—Benzimidazolylmethyl) hydroquinones" Chemical Abstracts Service, Database accession No. 1969: 115062 (1984).
Bartha et al., "Preparation of herbicidal aryloxypropionates", Chemical Abstracts Service, Database accession No. 1990:17758 (1990).
Cole et al., "Anti-Infective Innovations: Highlights from the 49th Interscience Conference on Antimicrobial Agents and Chemotherapy", Drugs of the Future 2009 Prous Science ESP, 34(12): 1005-1028 (2009).
Lesyk et al., New 5-substituted thiazolo[3,2-b][1,2,4]triazol-6-ones: Synthesis and anticancer evaluation: European Journal of Medicinal Chemistry, 42: 641-648 (2007).
PubChem Compound Summary CID 24474227. 2-(2,4-dichlorophenoxy)-N-[4-(dimethylamino)phenyl]methyl]acetamide. 2008 [Retrieved from the Internet Jan. 2, 2012: http://pubchem.ncbi.nlm.nih.gov/summary.cgi?cid=24474227&loc=ec_rcs].

* cited by examiner

*Primary Examiner* — Heidi Reese
(74) *Attorney, Agent, or Firm* — Yankwich & Associates, P.C.; Leon R. Yankwich; Michael R. Wesolowski

(57) ABSTRACT

Organic compounds showing the ability to inhibit effector toxin secretion or translocation mediated by bacterial type III secretion systems are disclosed. The disclosed type III secretion system inhibitor compounds are useful for combating infections by Gram-negative bacteria such as *Salmonella* spp., *Shigella flexneri*, *Psendomonas* spp., *Yersinia* spp., en tero pathogenic and enteroinvasive *Escherichia* coli, and *Chlamydia* spp. having such type III secretion systems.

14 Claims, 4 Drawing Sheets

SEQUENCE LISTING

```
<160> NUMBER OF SEQ ID NOS: 12

<210> SEQ ID NO 1
<211> LENGTH: 29
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 1
tactacgaat tcccaggaag caccgaagg                                             29

<210> SEQ ID NO 2
<211> LENGTH: 32
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 2
cattacgaat tcctggtact cgccgttggt at                                         32

<210> SEQ ID NO 3
<211> LENGTH: 20
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 3
tagggaaagt ccgctgtttt                                                       20

<210> SEQ ID NO 4
<211> LENGTH: 20
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 4
cctgaggtag ccattcatcc                                                       20

<210> SEQ ID NO 5
<211> LENGTH: 48
<212> TYPE: DNA
<213> ORGANISM: Artificial Sequence
<220> FEATURE:
```

```
<223> OTHER INFORMATION: oligonucleotide primer for P. aeruginosa gene
      amplification

<400> SEQUENCE: 5
tacaaaaaag caggctagga aacagacatg catattcaat cgcttcag                    48

<210> SEQ ID NO 6
<211> LENGTH: 51
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 6
atcttttact ttcaccagcg tttctgggtg accgtcggcc gatactctgc t                51

<210> SEQ ID NO 7
<211> LENGTH: 20
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 7
cacccagaaa cgctggtgaa                                                   20

<210> SEQ ID NO 8
<211> LENGTH: 38
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 8
tacaagaaag ctgggtttgg tctgacagtt accaatgc                               38

<210> SEQ ID NO 9
<211> LENGTH: 29
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 9
ggggacaagt ttgtacaaaa aagcaggct                                         29

<210> SEQ ID NO 10
<211> LENGTH: 29
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 10
ggggaccact ttgtacaaga aagctgggt                                         29

<210> SEQ ID NO 11
<211> LENGTH: 72
<212> TYPE: DNA
<213> ORGANISM: Artificial Sequence
<220> FEATURE:
<223> OTHER INFORMATION: oligonucleotide primer for P. aeruginosa gene
```

```
                    amplification

<400> SEQUENCE: 11
tacaaaaaag caggctagga aacagctatg acgaagaaga tcagttttat aattaacggc        60
caggttgaaa tc                                                          72

<210> SEQ ID NO 12
<211> LENGTH: 36
<212> TYPE: DNA
<213> ORGANISM: Artificial Sequence
<220> FEATURE:
<223> OTHER INFORMATION: oligonucleotide primer for P. aeruginosa gene
      amplification

<400> SEQUENCE: 12
tacaagaaag ctgggtgttt tcccagtcac gacgtt                                36
```

INHIBITORS OF BACTERIAL TYPE III SECRETION SYSTEM

CROSS-REFERENCE TO RELATED APPLICATIONS

This application is a United States national stage filing under 35 U.S.C. §371 of international (PCT) application no. PCT/US2012/046676, filed Jul. 13, 2012, and designating the US, which claims priority to U.S. provisional patent application Ser. no. 61/507,259, filed Jul. 13, 2011.

STATEMENT REGARDING FEDERALLY SPONSORED RESEARCH

This invention was made with government support under grant AI068185 awarded by the National Institutes of Health. The government has certain rights in the invention.

FIELD OF THE INVENTION

This invention is in the field of therapeutic drugs to treat bacterial infection and disease. In particular, the invention provides organic compounds that inhibit the type III secretion system of one or more bacterial species.

BACKGROUND OF THE INVENTION

The bacterial type III secretion system (T3SS) is a complex multi-protein apparatus that facilitates the secretion and translocation of effector proteins from the bacterial cytoplasm directly into the mammalian cytosol. This complex protein delivery device is shared by over 15 species of Gram-negative human pathogens, including *Salmonella* spp., *Shigella flexneri*, *Pseudomonas aeruginosa*, *Yersinia* spp., enteropathogenic and enteroinvasive *Escherichia coli*, and *Chlamydia* spp. (Hueck, 1998, Type III protein secretion systems in bacterial pathogens of animals and plants, *Microbial. Biol. Rev.*, 62:379-433; Keyser, et al., 2008, Virulence blockers as alternatives to antibiotics: type III secretion inhibitors against Gram-negative bacteria, *J. Intern. Med.*, 264:17-29.) In the opportunistic pathogen *P. aeruginosa*, the T3SS is the major virulence factor contributing to the establishment and dissemination of acute infections (Hauser, 2009, The type III secretion system of *Pseudomonas aeruginosa*: infection by injection, *Nat. Rev. Microbial.*, 7:654-65). Four T3SS effectors have been identified in *P. aeruginosa* strains—ExoS, ExoT, ExoY, and ExoU. ExoS and ExoT are bifunctional proteins consisting of an N-terminal small G-protein activating protein (GAP) domain and a C-terminal ADP ribosylation domain; ExoY is an adenylate cyclase; and ExoU is a phospholipase (see review in Engel and Balachandran, 2009, Role of *Pseudomonas aeruginosa* type III effectors in disease, *Curr. Opin. Microbiol.*, 12:61-6).

In studies with strains producing each effector separately, ExoU and ExoS contributed significantly to persistence, dissemination, and mortality while ExoT produced minor effects on virulence in a mouse lung infection model, and ExoY did not appear to play a major role in the pathogenesis of *P. aeruginosa* (Shaver and Hauser, 2004, Relative contributions of *Pseudomonas aeruginosa* ExoU, ExoS, and ExoT to virulence in the lung, *Infect. Immum.*, 72:6969-77). While not a prototypical effector toxin, flagellin (FliC) may also be injected into the cytoplasm of host cells from *P. aeruginosa* via the T3SS machinery, where it triggers activation of the innate immune system through the nod-like receptor NLRC4 inflammasome. (Franchi, et al., 2009, The inflammasome: a caspase-1-activation platform that regulates immune responses and disease pathogenesis, *Nat. Immunol.*, 10:241-7; Miao, et al., 2008, *Pseudomonas aeruginosa* activates caspase 1 through 1paf, *Proc. Natl. Acad. Sci. USA*, 105: 2562-7.)

The presence of a functional T3SS is significantly associated with poor clinical outcomes and death in patients with lower respiratory and systemic infections caused by *P. aeruginosa* (Roy-Burman, et al., 2001, Type III protein secretion is associated with death in lower respiratory and systemic *Pseudomonas aeruginosa* infections, *J. Infect. Dis.*, 183:1767-74). In addition, T3SS reduces survival in *P. aeruginosa* animal infection models (Schulert, et al., 2003, Secretion of the toxin ExoU is a marker for highly virulent *Pseudomonas aeruginosa* isolates obtained from patients with hospital-acquired pneumonia, *J. Infect. Dis.*, 188:1695-706), and is required for the systemic dissemination of *P. aeruginosa* in a murine acute pneumonia infection model (Vance, et al., 2005, Role of the type III secreted exoenzymes S, T, and Y in systemic spread of *Pseudomonas aeruginosa* PAO1 in vivo, *Infect. Immun.*, 73:1706-13). T3SS appears to contribute to the development of severe pneumonia by inhibiting the ability of the host to contain and clear bacterial infection of the lung. Secretion of T3SS toxins, particularly ExoU, blocks phagocyte-mediated clearance at the site of infection and facilitates establishment of an infection (Diaz, et al., 2008, *Pseudomonas aeruginosa* induces localized immunosuppression during pneumonia, *Infect, Immun.*, 76:4414-21). The result is a local disruption of an essential component of the innate immune response, which creates an environment of immunosuppression in the lung. This not only allows *P. aeruginosa* to persist in the lung, but it also facilitates superinfection with other species of bacteria.

While several antibacterial agents are effective against *P. aeruginosa*, the high rates of mortality and relapse associated with serious *P. aeruginosa* infections, even in patients with hospital-acquired pneumonia (HAP) receiving antibiotics active against the causative strain, reflect the increasing incidence of drug-resistant strains and highlights the need for new therapeutic agents. (See, e.g., El Solh, et al., 2007, Clinical and hemostatic responses to treatment in ventilator-associated pneumonia: role of bacterial pathogens, *Crit. Care Med.*, 35:490-6; Rello, et al., 1998, Recurrent *Pseudomonas aeruginosa* pneumonia in ventilated patients: relapse or reinfection?, *Am. J. Respir. Crit. Care Med.*, 157:912-6; and Silver, et al., 1992, Recurrent *Pseudomonas aeruginosa* pneumonia in an intensive care unit., *Chest*, 101:194-8.) Conventional bacteriostatic and bactericidal antibiotics appear insufficient to adequately combat these infections, and new treatment approaches such as inhibitors of *P. aeruginosa* virulence determinants may prove useful as adjunctive therapies. Veesenmeyer, et al., 2009, *Pseudomonas aeruginosa* virulence and therapy: evolving translational strategies, *Crit. Care Med.*, 37:1777-86.

The potential for the type III secretion system as a therapeutic target has prompted several groups to screen for inhibitors of T3SS in various bacterial species, including *Salmonella typhimurium, Yersinia pestis, Y. pseudotuberculosis*, and *E. coli*. (Reviewed in Keyser, et al., 2008, Virulence blockers as alternatives to antibiotics: type III secretion inhibitors against Gram-negative bacteria, *J. Intern. Med.*, 264:17-29; and Clatworthy, et al., 2007, Targeting virulence: a new paradigm for antimicrobial therapy, *Nat. Chem. Biol.*, 3:541-8). High levels of sequence conservation among various proteins comprising the T3SS apparatus suggest that inhibitors of T3SS in one species may also be active in related species. Broad spectrum activity of T3SS inhibitors identified in a screen against *Yersinia* has been demonstrated in *Salmonella, Shigella,* and *Chlamydia.* Hudson, et al., 2007. Inhibition of type III secretion in *Salmonella enterica* serovar Typhimurium by small-molecule inhibitors, *Antimicrob. Agents Chemother.,* 51:2631-5; Veenendaal, et al., 2009, Small molecule type III secretion system inhibitors block assembly of the *Shigella* type III secreton, *J. Bacteriol.,* 191:563-70; Wolf, et al., 2006, Treatment of *Chlamydia trachomatis* with a small molecule inhibitor of the *Yersinia* type III secretion system disrupts progression of the chlamydial developmental cycle, *Mol. Microbiol.,* 61:1543-55.

Screening for *P. aeruginosa* T3SS inhibitors has been reported, leading to several selective inhibitors of *P. aeruginosa.* T3SS-mediated secretion, one of which reproducibly inhibits both T3SS-mediated secretion and translocation. Aiello, et al., 2010, Discovery and Characterization of Inhibitors of *Pseudomonas aeruginosa* Type III Secretion, *Antimicrob. Agents Chemother.,* 54(5): 1988-1999.

Clearly, needs remain for new, potent inhibitors of bacterial T3SS of *P. aeruginosa* and other bacterial species.

SUMMARY OF THE INVENTION

The present invention provides novel antibacterial/anti-virulence agents active against current drug-resistant strains of *P. aeruginosa* and some other Gram-negative pathogens. The compounds of the invention show a level of potency in comparison to previously reported T3SS inhibitor compounds that make them promising additions to the developing family of antibacterial agents.

The present invention provides new bacterial type III secretion system (T3SS) inhibitor compounds. The T3SS inhibitory compounds described herein were identified through a program to make structural modifications on a phenoxyacetamide scaffold, and then to test the novel analogs using cell-based secretion, translocation and cytotoxicity assays. As reported in Aiello, et al., 2010, op. cit., structure/activity relationship (SAR) studies based on the compound designated MBX-1641, i.e., N-(benzo[d][1,3]dioxol-5-ylmethyl)-2-(2,4-dichlorophenoxy)propanamide, having the formula

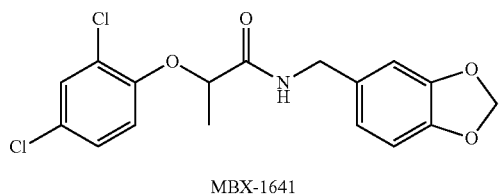 [SMILES: CC(Oc1ccc(Cl)cc1Cl)C(=O)NCc1ccc2c(c1)OCO2]

MBX-1641 led to the synthesis of additional T3SS inhibitor analogs but none that led to optimization of potency and selectivity in blocking both T3SS-mediated secretion and translocation of *P. aeruginosa* effectors or to significant reduction of cytotoxicity.

The present invention is the result of further SAR study of the phenoxyacetamide scaffold. The results provide significant increases in potency (3-4 fold), provide decreases in cytotoxicity (>3-fold), and demonstrate important structure/activity relationships with respect to the prototypical inhibitor scaffold represented by MBX-1641. It has been discovered, for example, that an ethyl substituent at the asymmetric center, which will be referred to herein as the α (alpha) carbon in the illustrative aryl-linked acetamide scaffold formula below,

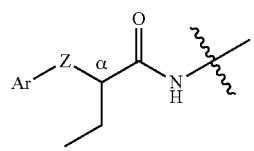

is an optimal hydrocarbon substituent on this scaffold and serves as a structural distinction from previously studied aryloxyacetamide inhibitor compounds.

Accordingly, the T3SS inhibitor compounds described herein inhibit T3SS-mediated secretion of a bacterial exotoxin (effector) from a bacterial cell. More preferably, a T3SS inhibitor compound described herein inhibits T3SS-mediated secretion of an effector from a bacterial cell and also inhibits T3SS-mediated translocation of the effector from the bacterial cell to a host cell (e.g., human or other animal cell).

In a preferred embodiment, a T3SS inhibitor compound described herein inhibits the T3SS in a bacterium of the genus *Pseudomonas, Yersinia,* or *Chlamydia.*

In another embodiment, a T3SS inhibitor compound described herein inhibits the T3SS of *Pseudomonas* and the T3SS of a bacterium of at least one other genus. Preferably, the inhibition target *Pseudomonas* bacterium is *P. aeruginosa.* Preferably, the other bacterial genus susceptible to T3SS inhibition by compound(s) of the invention is *Yersinia* or *Chlamydia.* A preferred inhibition target species of *Yersinia* is *Y. pestis.* A preferred inhibition target species of *Chlamydia* is *C. trachomatis.*

The present invention provides a family of bacterial type III secretion system (T3SS) inhibitor compounds of formula I:

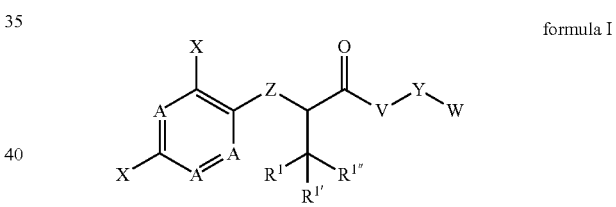

formula I wherein,

A is independently CH or N;

X is independently selected from hydrogen or halogen;

Z is O, S, NH; or $NR^3$, wherein $R^3$ is alkyl;

$R^1$, $R^{1'}$, and $R^{1''}$ are selected independently from: hydrogen, halogen, alkyl, hydroxy, alkoxy, alkylthio, or cyano, wherein no more than two of the preceding radicals is hydrogen;

V is $NR^2$, O, or $CR^3R^4$;

$R^2$, $R^3$, and $R^4$ are independently hydrogen or alkyl;

Y is selected from:

a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamide, aminosulfonyl, alkylsulfonyl, aryl, heteroaryl, alkoxy, alkylthio; aryloxy, and heteroaryloxy;

oxygen;

or $NR^5$ where $R^5$ is hydrogen or alkyl;

W is an aryl or heteroaryl radical forming a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy, and wherein any two substituents together may form an aromatic or non-aromatic ring structure fused with said aryl or heteroaryl radical W, which substituents found on W also may be optionally bonded covalently to either Y or $R^2$, or both Y and $R^2$, to form heterocyclic or carbocyclic ring systems, which ring systems may be aromatic, heteroaromatic, or partly aromatic, (that is, one or more rings being aromatic and one or more rings being non-aromatic (saturated)).

In another embodiment, the present invention provides a family of bacterial type III secretion system (T3SS) inhibitor compounds of formula II:

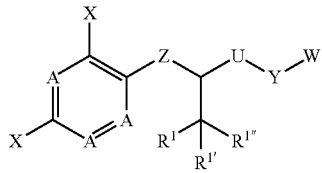

formula II wherein
A is independently CH or N;
X is independently selected from hydrogen or halogen;
Z is O, S, NH; or $NR^3$, where $R^3$ is alkyl;
$R^1$, $R^{1'}$, and $R^{1''}$ are selected independently from: hydrogen, halogen, alkyl, hydroxy, alkoxy, alkylthio, or cyano, wherein no more than two of the preceding radicals is hydrogen;
$R^2$, $R^3$, and $R^4$ are independently hydrogen or alkyl;
U is a divalent 5- or 6-membered heterocyclic ring selected from: oxazole, oxazoline, isoxazole, isoxazoline, 1,2,3 triazole, 1,2,4-triazole, 1,2,4-oxadiazole, 1,3,4-oxadiazole, 1,2-oxazine, 1,3-oxazine, pyrimidine, pyridazine, pyrazine,
Y is selected from:
a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy;
oxygen;
or $NR^5$ where $R^5$ is hydrogen or alkyl;
W is an aryl or heteroaryl radical forming a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy, and wherein any two substituents together may form an aromatic or non-aromatic ring structure fused with said aryl or heteroaryl radical W, which substituents found on W also may be optionally bonded covalently to either Y or $R^2$, or both Y and $R^2$, to form heterocyclic or carbocyclic ring systems, which ring systems may be aromatic, heteroaromatic, or partly aromatic (that is, one or more rings being aromatic and one or more rings being non-aromatic (saturated)).

In another embodiment, the present invention provides a T3SS inhibitor compound of formula III:

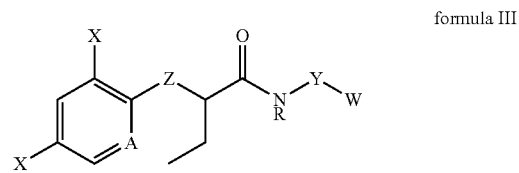

formula III wherein
A is CH or N;
X is independently selected from hydrogen or halogen;
R is hydrogen or methyl;
Y is a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy;
Z is O, S, or NH or $NR^3$; and
W is an aryl or heteroaryl radical forming a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, hydroxyl, amino, carboxamido, carboxyl, cyano, sulfonamido, sulfonyl, alkyl, alkenyl, alkynyl, cycloalkyl, heterocycloalkyl, aryl, heteroaryl, alkoxy, alkylthio, aryloxy, and heteroaryloxy, and wherein any two substituents together may form an aromatic or non-aromatic ring structure fused with said aryl or heteroaryl radical W, which substituents found on W also may be optionally bonded covalently to either Y or $R^2$, or both Y and $R^2$, to form heterocyclic or carbocyclic ring systems, which ring systems may be aromatic, heteroaromatic, or partly aromatic (that is, one or more rings being aromatic and one or more rings being non-aromatic (saturated)).

In yet another embodiment, the present invention provides a T3SS inhibitor compound of formula III, wherein
A is CH or N;
at least one X is Cl and the other X is hydrogen, F, or Cl;
Y is —$CH_2$—, —$CH(CH_3)$—, or —$C(CH_3)_2$—; and
W is selected from

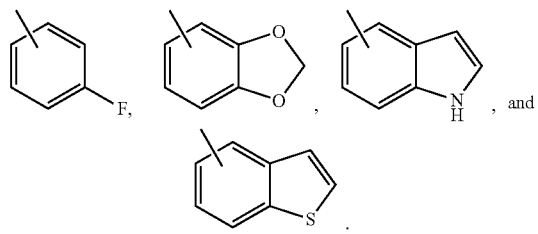

Of particular interest are compounds of the foregoing formulae I, II and III that are racemic mixtures of the R- and S-isomers or the isolated R-isomer, considering the asymmetric carbon (α carbon). Thus, preferred compounds will be isolated R-isomers denoted by the formulae Ia, IIa, or IIIa, below:

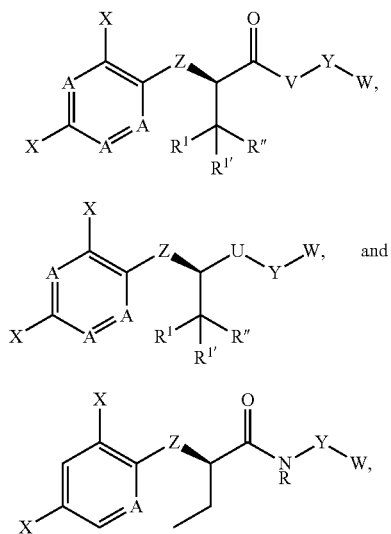

formula Ia formula IIa formula IIIa wherein A, X, Y, Z and W have the same values as recited for formulae I, II, III, respectively, above.

Compounds according to the foregoing formulae were tested using assays showing specific inhibition of the T3SS of *P. aeruginosa*. Selected compounds were additionally tested for inhibition of *Chlamydia trachomatis* and *Yersinia pestis* and showed effective inhibition, indicating that a T3SS inhibitor compound according to this invention can be an effective inhibitor of many bacterial type III secretion systems, acting across species within a genus and across genera of bacteria having type III secretion systems.

T3SS inhibitor compounds described herein inhibit T3SS effector transcription by at least 15% at a concentration of 50 µM using a transcriptional reporter assay or exhibit at least 50% inhibition of effector secretion at a concentration of 100 µM or less ($IC_{50} \leq 100$ µM) in an effector secretion assay. The compounds described above show T3SS-specific inhibition in *Pseudomonas* of greater than 15% using an exoT-lux transcriptional reporter construct transferred into *Pseudomonas aeruginosa* PAO1 (reporter strain MDM852, described herein) and/or show an $IC_{50}$ of less than 100 µM for T3SS as measured in an assay of T3SS-mediated secretion of an effector toxin-β-lactamase reporter fusion protein assay described herein using *P. aeruginosa* strain MDM973 (PAK/pUCP24GW-lacI$^Q$-lacPO-exoS::blaM). See Table 1, infra. Compounds inhibiting effector transcription by less than 15% or with an $IC_{50}$ greater than 200 µM are not generally useful as T3SS inhibitors in the compositions and methods described herein.

In a particularly preferred embodiment, a T3SS inhibitor compound useful in the compositions and methods described herein has an $IC_{50}$ value of less than 200 µM as measured in a T3SS-mediated effector toxin-β-lactamase reporter fusion protein secretion assay described herein (or comparable assay) and also has a relatively low cytotoxicity toward human cells, such as a $CC_{50}$ value of greater than or equal to 200 µM ($CC_{50} \geq 200$ µM) as measured in a standard cytotoxicity assay as described herein or as employed in the pharmaceutical field for antibiotics. Such standard cytotoxicity assays may employ any human cell typically employed in cytotoxicity assays for antibiotics, including but not limited to, Chinese hamster ovary (CHO) cells, HeLa cells, Hep-2 cells, human embryonic kidney (HEK) 293 cells, 293T cells, and the like.

Even more preferably, a T3SS inhibitor compound described herein has an $IC_{50}$ value ≤50 µM as measured in a T3SS-mediated effector toxin-β-lactamase reporter fusion protein secretion assay as described herein or in a comparable assay.

In a particularly preferred embodiment of the invention, a T3SS inhibitor compound blocks T3 SS-mediated secretion and translocation of one or more toxin effectors from cells of *P. aeruginosa*.

The T3SS compounds described herein are useful as anti-virulence agents and may be used to treat bacterial infections. Accordingly, an individual infected with or exposed to bacterial infection, especially *Pseudomonas, Yersinia* or *Chlamydia* infection, may be treated by administering to the individual in need an effective amount of a compound according to the invention.

Use of one or more or a combination of the compounds disclosed herein to treat infection by bacteria having a type III secretion system is contemplated herein. Especially, use of one or more or a combination of the above compounds to treat *Pseudomonas, Yersinia* or *Chlamydia* infection is contemplated herein. In particular, use of one or more or a combination of the above compounds for the treatment of *Pseudomonas aeruginosa, Yersinia pestis,* or *Chlamydia trachomatis* infections is advantageously carried out by following the teachings herein.

The present invention also provides pharmaceutical compositions containing one or more of the T3SS inhibitor compounds disclosed herein and a pharmaceutically acceptable carrier or excipient. The use of one or more of the T3SS inhibitor compounds in the preparation of a medicament for combating bacterial infection is disclosed.

A T3SS inhibitor compound or combination of T3SS inhibitor compounds described herein may be used as a supporting or adjunctive therapy for the treatment of bacterial infection in an individual (human or other animal). In the case of an individual with a healthy immune system, administration of a T3SS inhibitor compound described herein to inhibit the T3SS of bacterial cells in or on an individual may be sufficient to permit the individual's own immune system to effectively clear or kill infecting or contaminating bacteria from the tissue of the individual. Alternatively, a T3SS inhibitor compound described herein may be administered to an individual in conjunction (i.e., in a mixture, sequentially, or simultaneously) with an antibacterial agent, such as an antibiotic, an antibody, or an immunostimulatory agent, to provide both inhibition of T3SS and inhibition of growth of invading bacterial cells.

In yet another embodiment, a composition comprising a T3SS inhibitor or a combination of T3SS inhibitors described herein may also comprise a second agent (second active ingredient, second active agent) that possesses a desired therapeutic or prophylactic activity other than that of T3SS inhibition. Such a second active agent includes, but is not limited to, an antibiotic, an antibody, an antiviral agent, an anticancer agent, an analgesic agent (e.g., a nonsteroidal anti-inflammatory drug (NSAID), acetaminophen, an opioid, a COX-2 inhibitor), an immunostimulatory agent (e.g., a cytokine), a hormone (natural or synthetic), a central nervous system (CNS) stimulant, an antiemetic agent, an anti-histamine, an erythropoietin, a complement stimulating agent, a sedative, a muscle relaxant agent, an anesthetic agent, an anticonvulsive agent, an antidepressant, an antipsychotic agent, and combinations thereof.

Compositions comprising a T3SS inhibitor described herein may be formulated for administration to an individual (human or other animal) by any of a variety of routes including, but not limited to, intravenous, intramuscular, subcutaneous, intra-arterial, parenteral, intraperitoneal, sublingual (under the tongue), buccal (cheek), oral (for swallowing), topical (epidermis), transdermal (absorption through skin and lower dermal layers to underlying vasculature), nasal (nasal mucosa), intrapulmonary (lungs), intrauterine, vaginal, intracervical, rectal, intraretinal, intraspinal, intrasynovial, intrathoracic, intrarenal, nasojejunal, and intraduodenal.

DETAILED DESCRIPTION OF THE INVENTION

Figure 1:
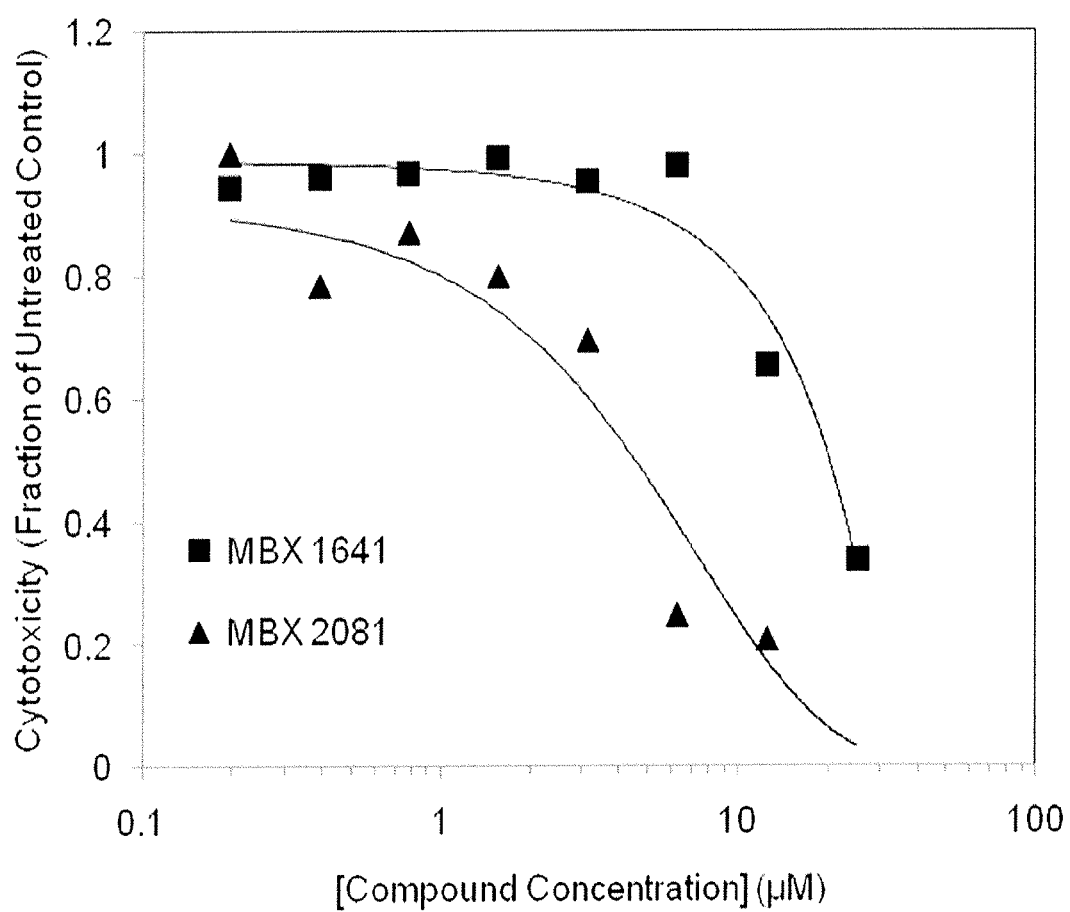
FIG. 1 is a graph illustrating concentration-dependent rescue of CHO cells from T3SS-mediated ExoU cytotoxicity by two phenoxyacetamide compounds, measured as previously described in Aiello, et al., 2010, *Antimicrob. Agents Chemother.*, 54:1988-99. A compound according to the invention, MBX-2081, is compared against a previously discovered T3SS inhibitor, designated MBX-1641, used as a standard of reference. The results indicate that MBX-2081 provides a 3-4-fold increase in potency compared to MBX-1641.

The invention provides organic compounds that inhibit a bacterial type III secretion system ("T3SS") that secretes and translocates bacterially produced effectors (also referred to as effector toxins, exotoxins, cytotoxins, bacterial toxins) from the bacterial cell into animal host cells. Effectors translocated into host cells can effectively inactivate the host immune response, such as by killing phagocytes and thereby disabling the host innate immune response. The T3SS is thus a critical virulence factor in establishing bacterial infections in an individual (human or other animal) and is particularly critical to *P. aeruginosa* opportunistic infections of human patients with compromised immune systems or that otherwise have been made susceptible to infection by bacteria such as *P. aeruginosa*.

That the invention may be more clearly understood, the following abbreviations and terms are used as defined below.

Abbreviations for various substituents (side groups, radicals) of organic molecules are those commonly used in organic chemistry. Such abbreviations may include "shorthand" forms of such substituents. For example, "Ac" is an abbreviation for an acetyl group, "Ar" is an abbreviation for an "aryl" group, and "halo" or "halogen" indicates a halogen radical (e.g., F, Cl, Br, I). "Me" and "Et" are abbreviations used to indicate methyl ($CH_3$—) and ethyl ($CH_3CH_2$—) groups, respectively; and "OMe" (or "MeO") and "OEt" (or "EtO") indicate methoxy ($CH_3O$—) and ethoxy ($CH_3CH_2O$—), respectively. Hydrogen atoms are not always shown in organic structural diagrams (e.g., at the end of a drawn line representing a $CH_3$ group) or may be only selectively shown in some structural diagrams, as the presence and location of hydrogen atoms in organic molecular structures are understood and known by persons skilled in the art. Likewise, carbon atoms are not always specifically abbreviated with "C", as the presence and location of carbon atoms in structural diagrams are known and understood by persons skilled in the art. Minutes are commonly abbreviated as "min"; hours are commonly abbreviated as "hr" or "h".

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or which "consists of") the named elements or steps to the exclusion of any other unnamed element or step. In any composition or method disclosed herein, known or disclosed equivalents of any named essential element or step may be substituted for that element or step. It is also understood that an element or step "selected from the group consisting of" refers to one or more of the elements or steps in the list that follows, including combinations of any two or more of the listed elements or steps.

The terms "bacterial type III secretion system inhibitor", "bacterial T3SS inhibitor", "bacterial T3SS inhibitor compound", and "T3SS inhibitor compound" as used herein are interchangeable and denote compounds exhibiting the ability to specifically inhibit a bacterial type III secretion system by at least 15% at a concentration of 50 μM, for example, as measured in a T3SS effector transcriptional reporter assay or the ability to inhibit a bacterial T3SS, for example, as measured in a T3SS-mediated effector toxin secretion assay.

In the context of therapeutic use of the T3SS inhibitor compounds described herein, the terms "treatment", "to treat", or "treating" will refer to any use of the T3SS inhibitor compounds calculated or intended to arrest or inhibit the virulence or the T3SS-mediated effector secretion or translocation of bacteria having type III secretion systems. Thus, treating an individual may be carried out after any diagnosis indicating possible bacterial infection, i.e., whether an infection by a particular bacterium has been confirmed or whether the possibility of infection is only suspected, for example, after exposure to the bacterium or to another individual infected by the bacterium. It is also recognized that while the inhibitors of the present invention affect the introduction of effector toxins into host cells, and thus block or decrease the virulence or toxicity resulting from infection, the inhibitor compounds are not necessarily bactericidal or effective to inhibit growth or propagation of bacterial cells. For this reason, it will be understood that elimination of the bacterial infection will be accomplished by the host's own immune system or immune effector cells, or by introduction of antibiotic agents. Thus, it is contemplated that the compounds of the present invention will be routinely combined with other active ingredients such as antibiotics, antibodies, antiviral agents, anticancer agents, analgesics (e.g., a nonsteroidal anti-inflammatory drug (NSAID), acetaminophen, opioids, COX-2 inhibitors), immunostimulatory agents (e.g., cytokines or a synthetic immunostimulatory organic molecules), hormones (natural, synthetic, or semisynthetic), central nervous system (CNS) stimulants, antiemetic agents, antihistamines, erythropoietin, agents that activate complement, sedatives, muscle relaxants, anesthetic agents, anticonvulsive agents, antidepressants, antipsychotic agents, and combinations thereof.

The term "partly aromatic" indicates that one or more rings are aromatic and one or more rings are non-aromatic (saturated).

The meaning of other terms will be understood by the context as understood by the skilled practitioner in the art, including the fields of organic chemistry, pharmacology, and microbiology.

The invention provides specific organic compounds that inhibit the T3SS of *Pseudomonas aeruginosa*. Structural analogs of previously studied T3SS inhibitors were evaluated for inhibition of T3SS-mediated secretion of an effector toxin-β-lactamase fusion protein (ExoS'-βLA) using *P. aeruginosa* strain MDM973 (PAK/pUCP24GW-lacI$^Q$-/lacPO-exoS::blaM, Table 1). See, Examples 1 and 2, below for details of screening and validation of initial T3SS inhibitors.

In a series of experiments to compare the effects of modifying the phenoxyacetamide scaffold, of which compound MBX-1641 is a prototypical example,

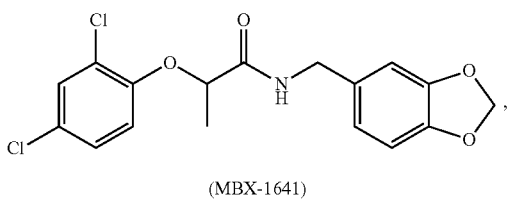 [SMILES: CC(Oc1ccc(Cl)cc1Cl)C(=O)NCc1ccc2c(c1)OCO2]

(MBX-1641)

analogs were synthesized having alterations to the "A" aryl group, to the linker of the A aryl group to the methyl acetamide moiety, to the "B" aryl group, and to the linker of the B aryl group to the methyl acetamide moiety (see Diagram 1), Diagram 1

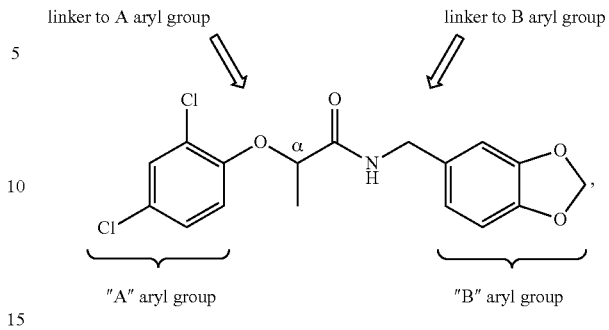

and the results indicated defined limitations to alternate structures on the methyl acetamide scaffold that would yield compounds also having specific inhibitory activity with respect to T3SS. Very few modifications of the A acyl group could be tolerated without raising inhibitory concentration levels ($IC_{50}$) beyond the minimal standard (i.e., 200 µM); however, a great range of substitutions for the B aryl group could be tolerated without adversely affecting and in some cases improving T3SS inhibitory performance. In general, the structure/activity relationships emerging from the experiments were characteristic of discoveries respecting alternative compounds reactive with a single target binding site. Alternate linker moieties to the A aryl group and the B aryl group were studied, and those positions were found to exhibit a significant influence on overall properties of the resulting compounds. Similarly, changes to eliminate the methyl group at the chiral center (α carbon) or to increase the size of the substituent group also led to significant effects on T3SS inhibitory properties.

From the program of analog synthesis and comparative testing a family of new compounds emerged which exhibited T3SS inhibitory properties comparable to and in many cases greater than the phenoxyacetamide inhibitor compounds that had been described previously. The family of new T3SS inhibitor compounds is defined by formula I:

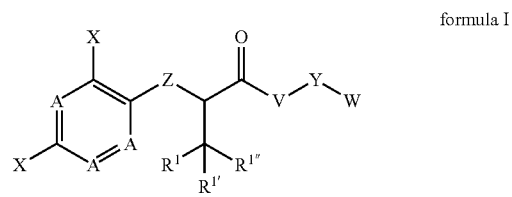

formula I wherein
A is independently CH or N;
X is independently selected from hydrogen or halogen;
Z is O, S, NH; or $NR^3$, wherein $R^3$ is alkyl;
$R^1$, $R^{1'}$, and $R^{1''}$ are selected independently from: hydrogen, halogen, alkyl, hydroxy, alkoxy, alkylthio, or cyano, wherein no more than two of the preceding radicals is hydrogen;
V is $NR^2$, O, or $CR^3R^4$;
$R^2$, $R^3$, and $R^4$ are independently hydrogen or alkyl;
Y is selected from:
a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy;

oxygen;

or $NR^5$ where $R^5$ is hydrogen or alkyl;

W is an aryl or heteroaryl radical forming a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, cyano, hydroxy, amino, alkylamino, carboxyl, alkoxycarbonyl, acylamino, amidino, sulfonamido, aminosulfonyl, alkylsulfonyl, aryl, heteroaryl, alkoxy, alkylthio; aryloxy, and heteroaryloxy, and wherein any two substituents together may form an aromatic or non-aromatic ring structure fused with said aryl or heteroaryl radical W, which substituents found on W also may be optionally bonded covalently to either Y or $R^2$, or both Y and $R^2$, to form heterocyclic or carbocyclic ring systems, which ring systems may be aromatic, heteroaromatic, or partly aromatic (that is, one or more rings being aromatic and one or more rings being non-aromatic (saturated)).

In another embodiment, the present invention provides a family of bacterial type III secretion system (T3SS) inhibitor compounds of formula II:

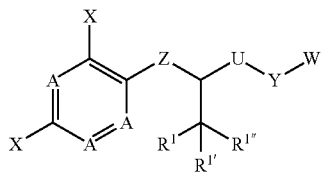

formula II wherein
A is independently CH or N;
X is independently selected from hydrogen or halogen;
Z is O, S, NH; or $NR^3$, wherein $R^3$ is alkyl;
$R^1$, $R^{1'}$, and $R^{1''}$ are selected independently from: hydrogen, halogen, alkyl, hydroxy, alkoxy, alkylthio, or cyano, wherein no more than two of the preceding radicals is hydrogen;
$R^2$, $R^3$, and $R^4$ are independently hydrogen or alkyl;
U is a divalent 5- or 6-membered heterocyclic ring selected from: oxazole, oxazoline, isoxazole, isoxazoline, 1,2,3 triazole, 1,2,4-triazole, 1,2,4-oxadiazole, 1,3,4-oxadiazole, 1,2-oxazine, 1,3-oxazine, pyrimidine, pyridazine, pyrazine,
Y is selected from:
a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio, aryloxy, and heteroaryloxy;

oxygen;

or $NR^5$ where $R^5$ is hydrogen or alkyl;

W is an aryl or heteroaryl radical forming a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy, and wherein any two substituents together may form an aromatic or non-aromatic ring structure fused with said aryl or heteroaryl radical W, which substituents found on W also may be optionally bonded covalently to either Y or $R^2$, or both Y and $R^2$, to form heterocyclic or carbocyclic ring systems, which ring systems may be aromatic, heteroaromatic, or partly aromatic (that is, one or more rings being aromatic and one or more rings being non-aromatic (saturated)).

In another embodiment, the present invention provides a T3SS inhibitor compound of formula III:

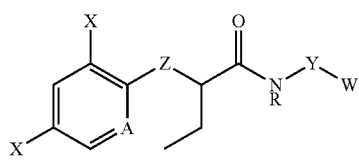

formula III wherein
A is CH or N;
X is independently selected from hydrogen or halogen;
R is hydrogen or methyl;
Y is a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, hetetoaryl, alkoxy, alkylthio; aryloxy, and heteroaryloxy;
Z is O, S, or NH or $NR^3$; and
W is an aryl or heteroaryl radical forming a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, hydroxyl, amino, carboxamide, carboxyl, cyano, sulfonamido, sulfonyl, alkyl, alkenyl, alkynyl, cycloalkyl, heterocycloalkyl, aryl, heteroaryl, alkoxy, alkylthio, aryloxy, and heteroaryloxy, and wherein any two substituents together may form an aromatic or non-aromatic ring structure fused with said aryl or heteroaryl radical W, which substituents found on W also may be optionally bonded covalently to either Y or $R^2$, or both Y and $R^2$, to form heterocyclic or carbocyclic ring systems, which ring systems may be aromatic, heteroaromatic, or partly aromatic (that is, one or more rings being aromatic and one or more rings being non-aromatic (saturated)).

In yet another embodiment, the present invention provides a T3SS inhibitor compound of formula III,
A is CH or N;
at least one X is Cl and the other X is hydrogen, F, or Cl;
Y is —$CH_2$—, —$CH(CH_3)$—, or —$C(CH_3)_2$—; and
W is selected from

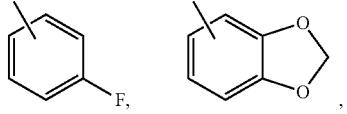

-continued

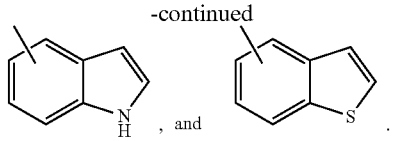, and

Of particular interest are compounds of the foregoing formulae I, II and III that are racemic mixtures of the R- and S-isomers or the isolated R-isomer, considering the asymmetric carbon (α carbon). Thus, preferred compounds will be isolated R-isomers denoted by the formulae Ia, IIa, or IIIa, below:

formula IIa

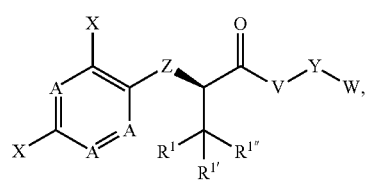

formula IIa

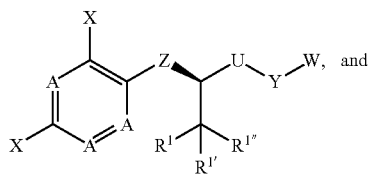, and formula IIIa

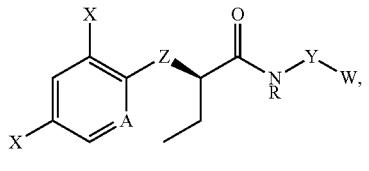

wherein A, X, Y, Z, and W have the same values as recited for formulae I, II, III, respectively, above.

Particular embodiments of the present invention include the following:

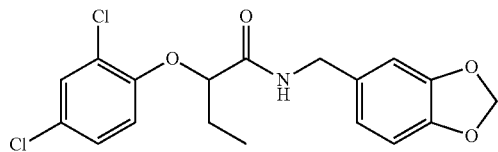 [SMILES: CCC(Oc1ccc(Cl)cc1Cl)C(=O)NCc1ccc2c(c1)OCO2]

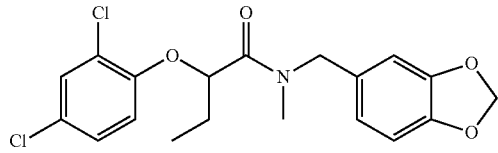

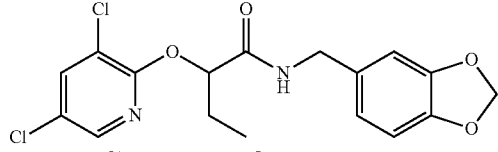

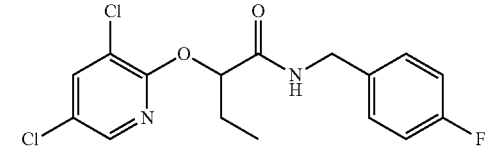

-continued

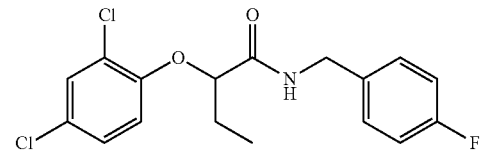

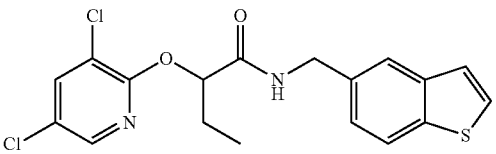

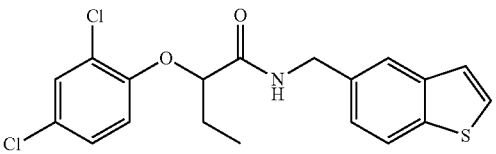

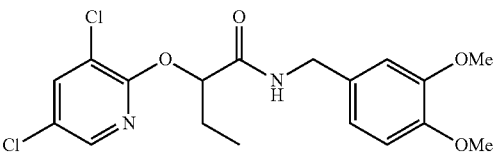

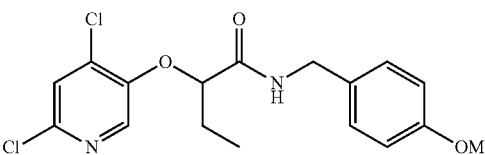

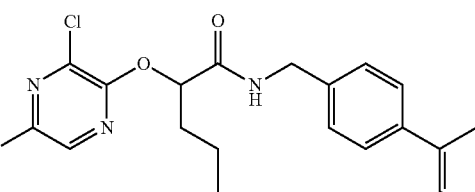

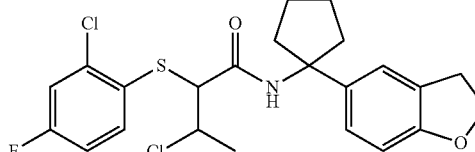

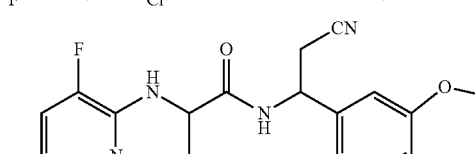

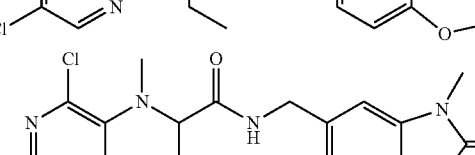

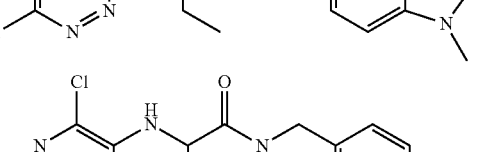

-continued
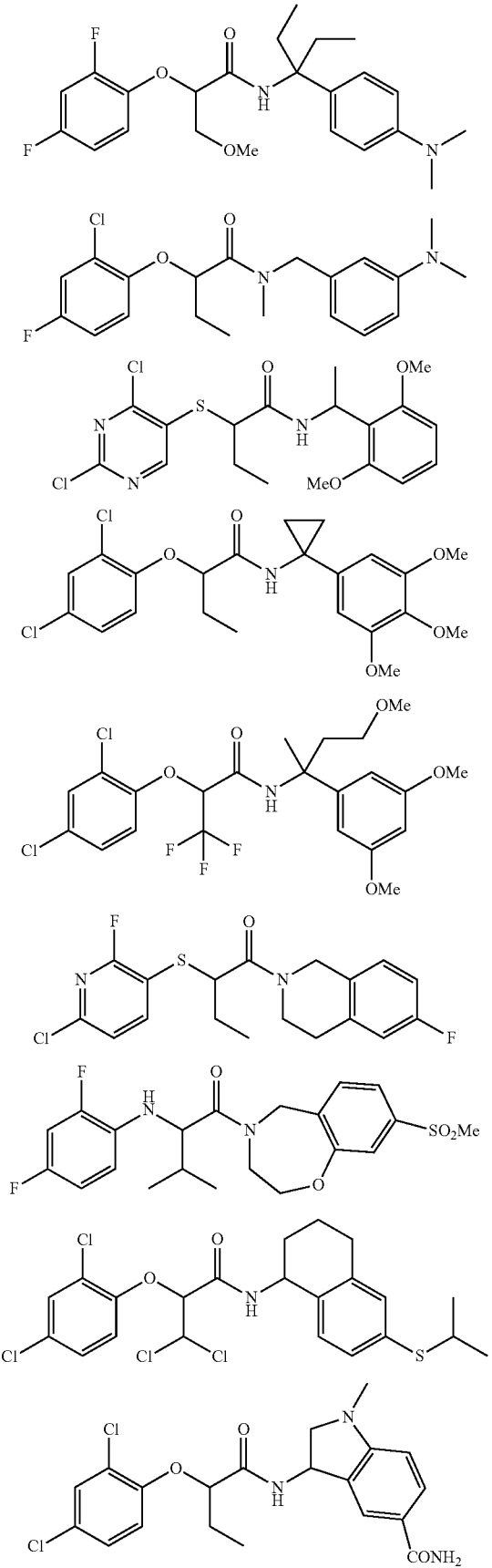
-continued
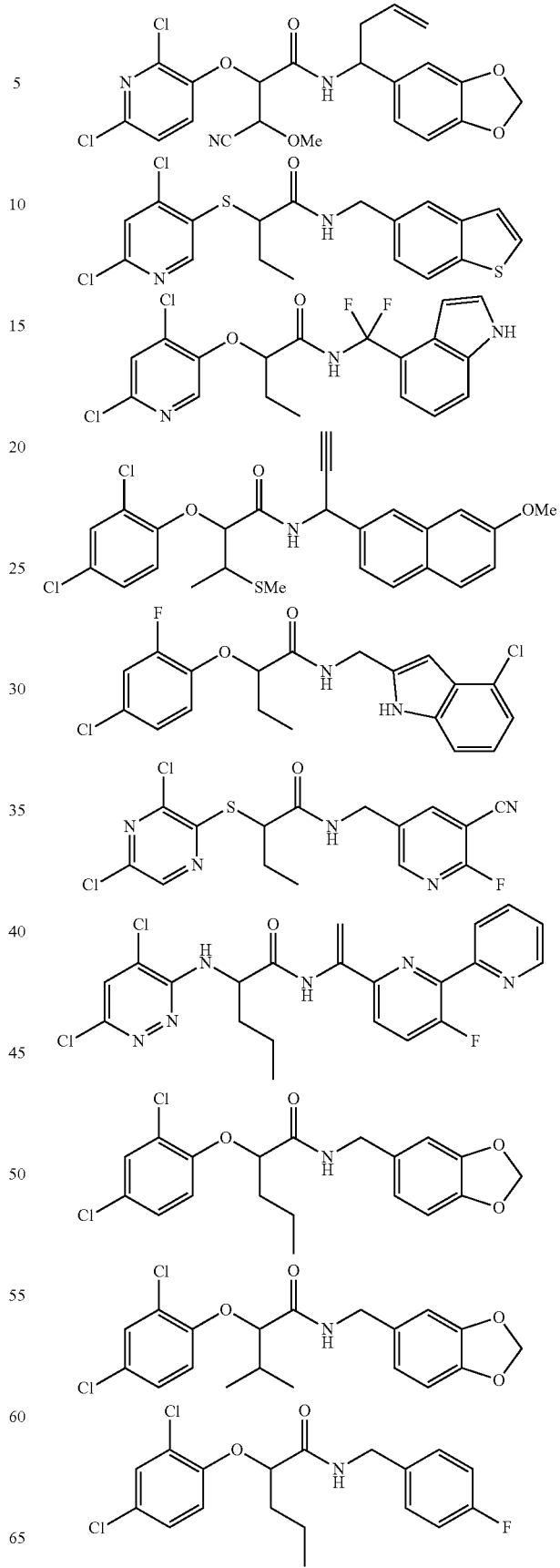

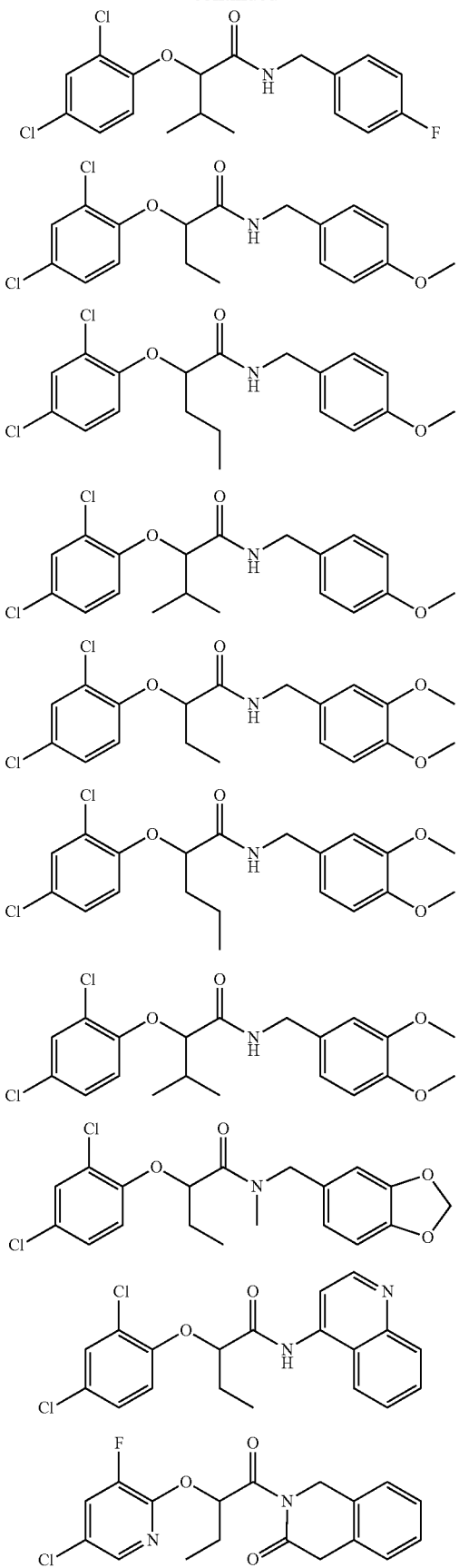
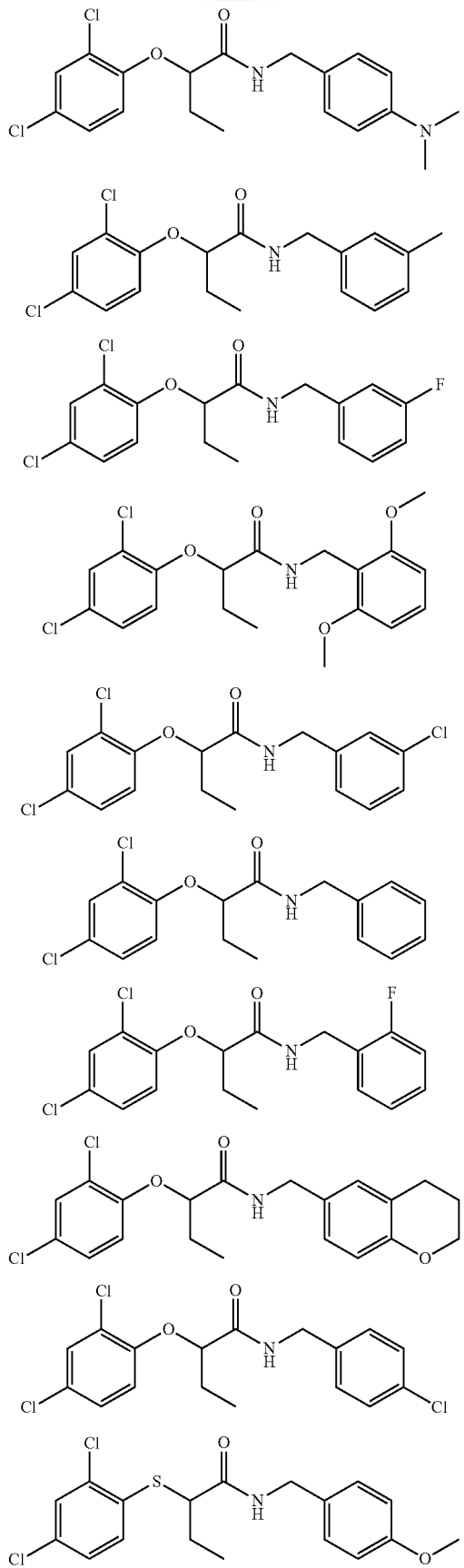

-continued
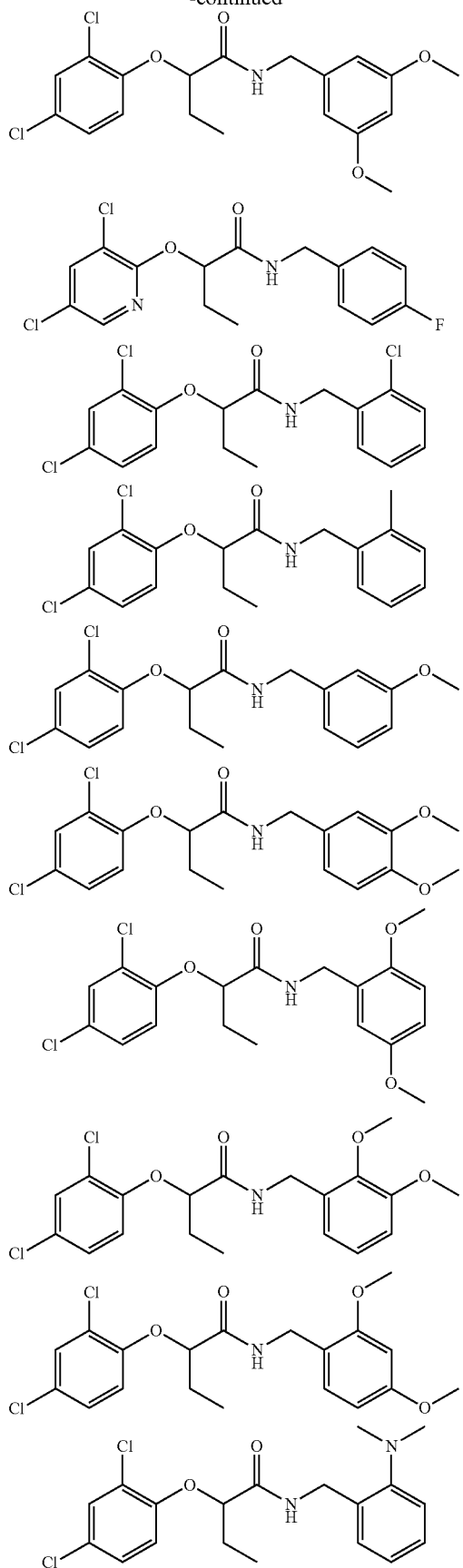
-continued
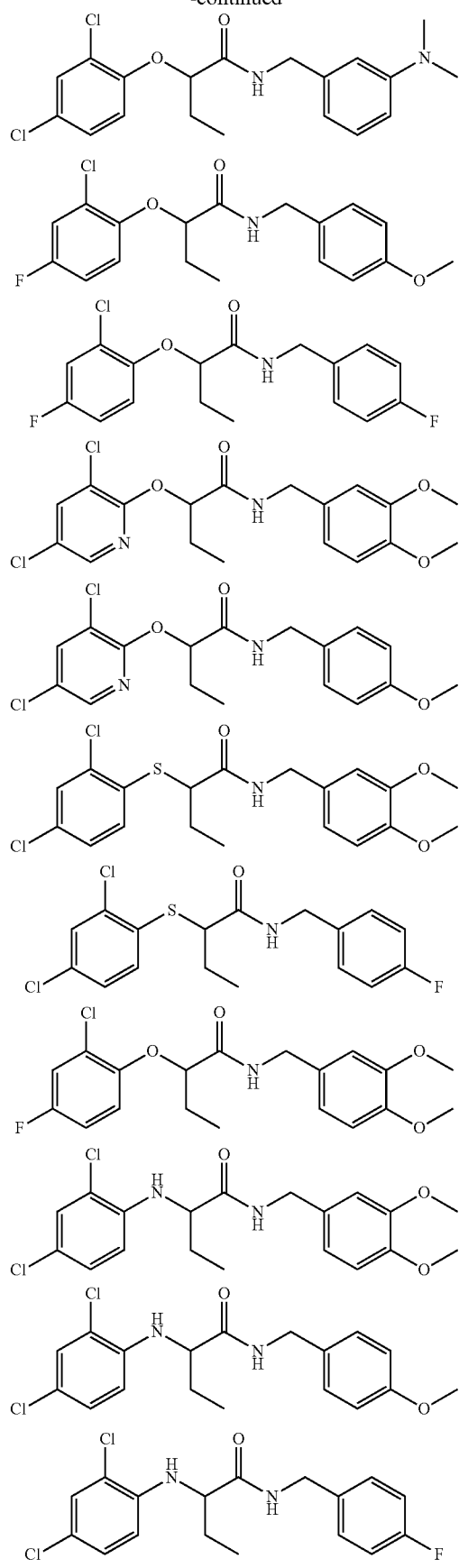

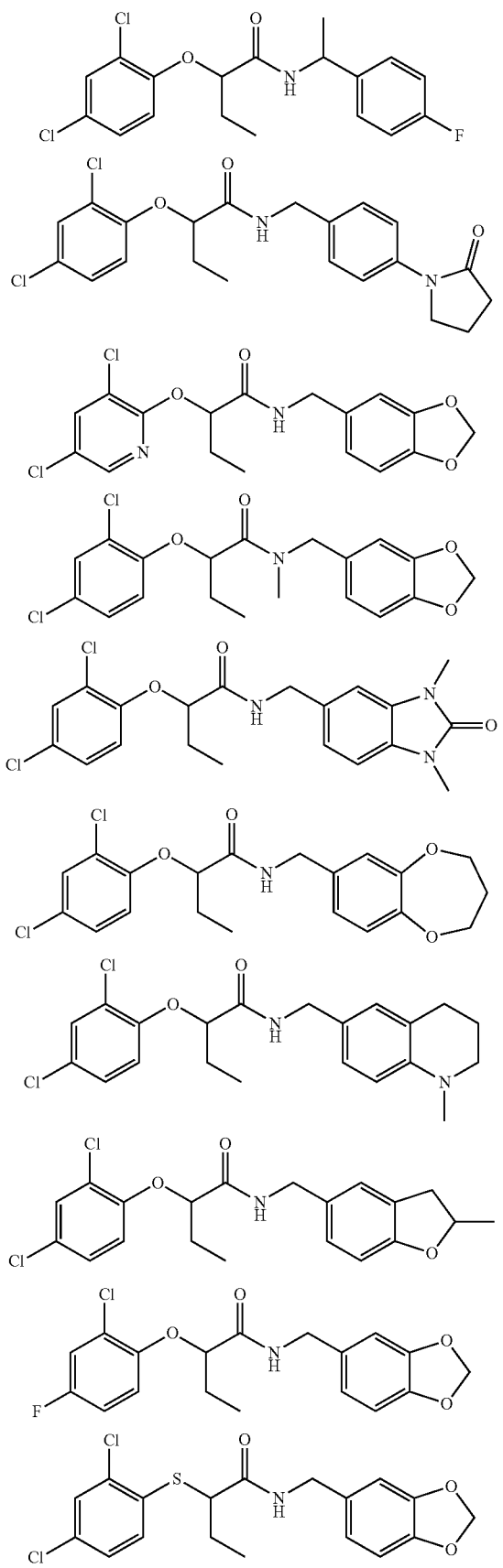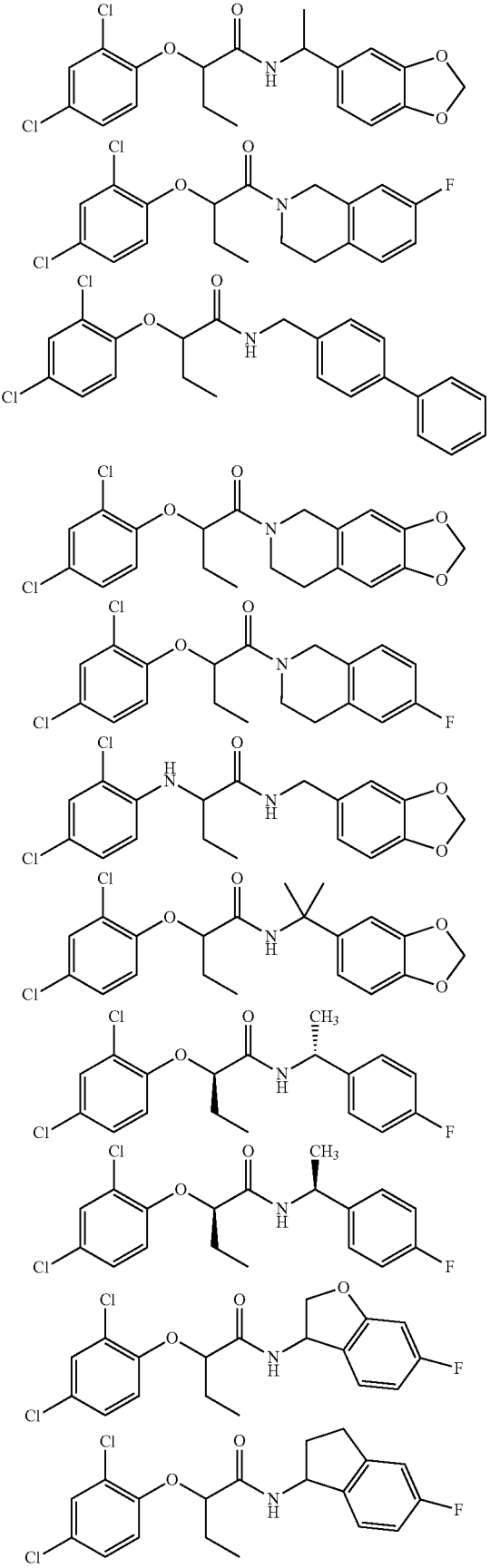

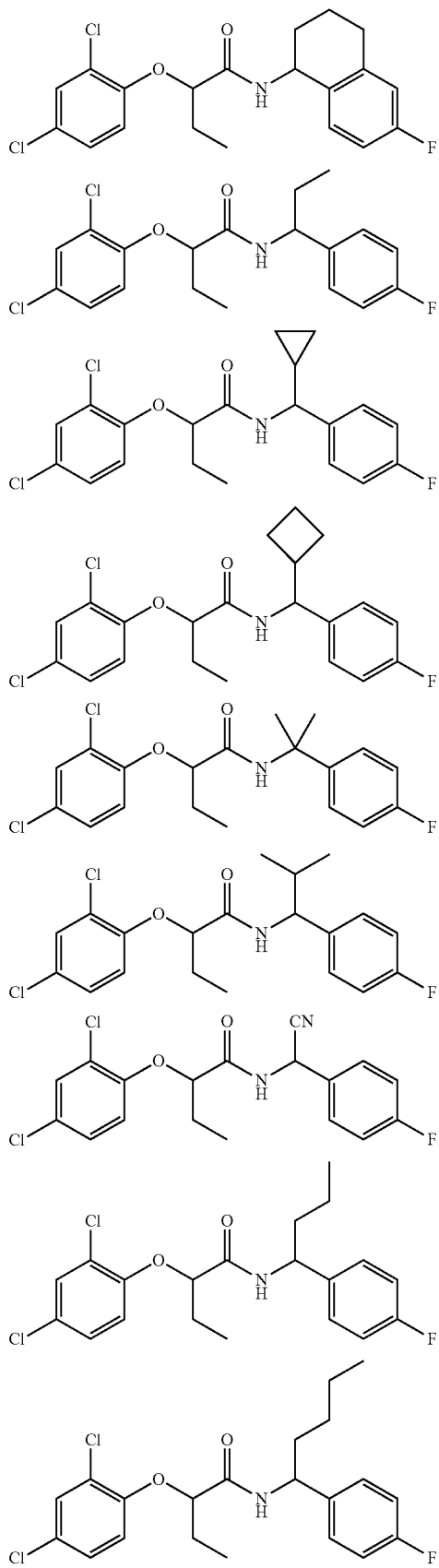
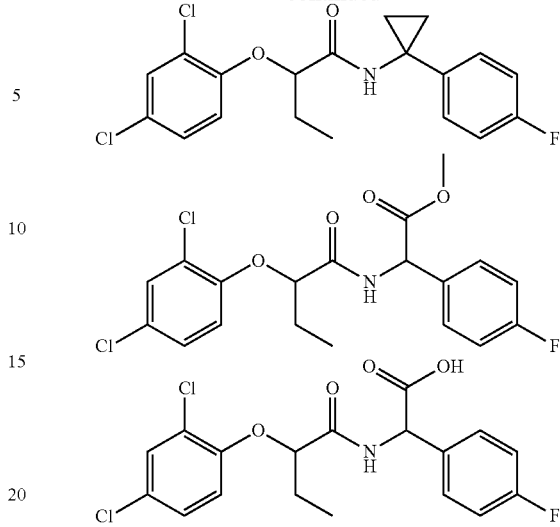

as well as particular isomeric forms of any of the foregoing.

The compounds of the present invention are designed to function by a novel antivirulence approach of potentiating the activity of existing antibacterial agents by bolstering the host innate immune system rather than directly killing invading bacteria. While not classic innate immune modulators, these anti-T3SS agents are believed to act indirectly on host targets by protecting the phagocytes of the innate immune system from most of the acute cytotoxic effects of bacteria having type III secretion systems such as *P. aeruginosa*. As therapeutic agents, the compounds of the invention may reduce the frequency of polymicrobial VAP infections, which appear to be due to local innate immune suppression by *P. aeruginosa* T3SS effector toxins. Diaz, et al., 2008, *Pseudomonas aeruginosa* induces localized immunosuppression during pneumonia, *Infect. Immun.*, 76:4414-21. Furthermore, these compounds of the present invention are species-specific and consequently spare normal flora, advantageously aligning this therapeutic approach with an emerging understanding of the protective role of the normal flora in infectious diseases. Parillo and Dellinger, *Critical Care Medicine: Principles of Diagnosis and Management in the Adult*, $2^{nd}$ ed. (Moseby, New York 2007), pp. 800-802.1. If applied in combination with an antibacterial agent, the new T3SS inhibitor compounds will not contribute to the elimination of normal flora and may permit the use of lower doses of co-administered antibiotics. Finally, these T3SS inhibitor compounds are equally potent against multiple *P. aeruginosa* strains (including clinical isolates), are not affected by *P. aeruginosa* efflux mechanisms, and are expected to exert no selection pressure for the development of resistance outside the body and only relatively weak selection pressure during therapy. This combination of favorable features of the compounds together with the novel mechanism of action provides a new approach to improve the treatment and prevention of acute *P. aeruginosa* infections such as VAP and bacteremia.

Inhibitor compounds of the present invention inhibit T3SS effector transcription by at least 15% at a concentration of 50 µM using a transcriptional reporter assay or by exhibiting at least 50% inhibition of effector secretion at a concentration of 100 µM or less ($IC_{50} \leq 100$ µM) in an effector secretion assay. The compounds listed above showed T3SS-specific inhibition in *Pseudomonas* of greater than 15% using an exoT-lux transcriptional reporter construct transferred into *Pseudomo-*

*nas aeruginosa* PAO1 (reporter strain MDM852, described herein) and/or showed an IC$_{50}$ value of less than 100 μM for T3SS as measured in an assay of T3SS-mediated secretion of an effector toxin-β-lactamase reporter fusion protein assay described herein using *P. aeruginosa* strain MDM973 PAK/ pUCP24GW-lacI$^Q$-lacPO-exoS::blaM) (Table 1). Compounds inhibiting effector transcription by less than 15% or with an IC$_{50}$ greater than 200 μM are not generally useful as T3SS inhibitors in the compositions and methods described herein.

In particularly preferred embodiments, a T3SS inhibitor compound useful in the compositions and methods described herein has an IC$_{50}$ value of less than 100 μM as measured in a T3SS-mediated effector toxin-β-lactamase reporter fusion protein secretion assay described herein (or comparable assay) and also has a relatively low cytotoxicity toward human cells, such as a CC$_{50}$ value of greater than or equal to 100 μM (CC$_{50}$≥100 μM) as measured in a standard cytotoxicity assay as described herein or as employed in the pharmaceutical field for antibiotics. Such standard cytotoxicity assays may employ any human cell typically employed in cytotoxicity assays for antibiotics, including but not limited to, Chinese hamster ovary (CHO) cells, HeLa cells, Hep-2 cells, human embryonic kidney (HEK) 293 cells, 293T cells, and the like.

Even more preferably, a T3SS inhibitor compound described herein has an IC$_{50}$ value ≤25 μM as measured in a T3SS-mediated effector toxin-β-lactamase reporter fusion protein secretion assay as described herein or in a comparable assay. Alternatively, preferred compounds of the present invention exhibit potency (IC$_{50}$) comparable or preferably greater than that of N-(benzo[d][1,3]dioxol-5-ylmethyl)-2-(2,4-dichlorophenoxy)propanamide (compound MBX-1641, described supra), which was used as an internal standard for comparison in the examples described below.

In yet another embodiment, a T3SS inhibitor compound described herein has a sufficiently high minimal inhibitory concentration (MIC) to indicate that it inhibits T3SS specifically.

Compositions and Methods

T3SS inhibitor compounds as described herein may also be synthesized using established chemistries. Most of the compounds described herein are produced or obtained as racemic mixtures of stereoisomers.

General Procedure

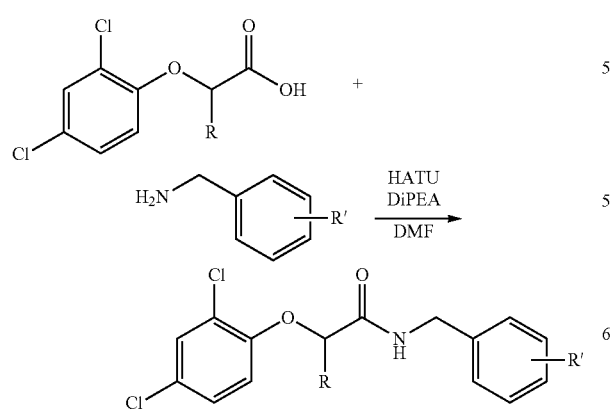

To a solution of substituted 2-(2,4-dichlorophenoxy)acetic acid in DMF are added 2-(1H-7-azabenzotriazol-1-yl)-1,1,3, 3-tetramethyl uronium hexafluorophosphate (1.2 eq), substituted benzylamine (1.2 eq), and diisopropylethylamine (1.3 eq). The solution is stirred at room temperature for 16 h. The reactions are diluted with water, extracted with EtOAc, and subjected to flash chromatography. Evaporation of solvent provides the desired product. The following compounds were prepared in the preceding manner:

(MBX 2081)

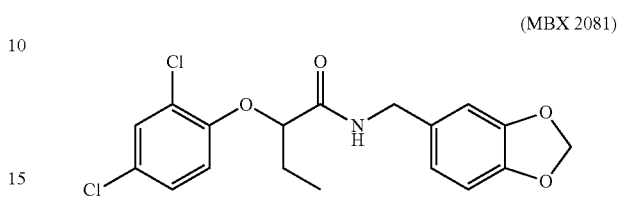

Light brown powder; R$_f$ 0.62 (50% EtOAc/hexanes); m.p. 110-114° C.; $^1$H-NMR [300 MHz, CDCl3]: δ 7.37 (d, 1H), 7.17 (dd, 1H), 6.82 (d, 2H), 6.72 (d, 2H), 6.67-6.65 (m, 2H), 5.94 (s, 2H), 4.61 (t, 1H) 4.32 (d, 2H), 2.08-1.99 (m, 2H), 1.04 (t, 3H); LCMS: 384.2 (M+1).

(MBX 2085)

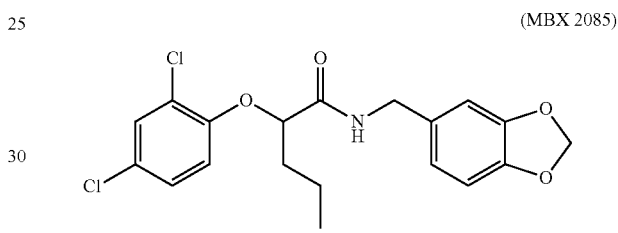

Light brown powder; R$_f$ 0.72 (50% EtOAc/hexanes); m.p. 91-94° C.; $^1$H-NMR [300 MHz, CDCl3]: δ 7.36 (d, 1H), 7.16 (dd, 1H), 6.83-6.71 (m, 3H), 6.65-6.63 (m, 2H), 5.94 (s, 2H), 4.63 (t, 1H) 4.35 (d, 2H), 2.10-1.93 (m, 2H), 1.59-1.48 (m, 2H), 0.95 (t, 3H); LCMS: 398.2 (M+1).

(MBX 2146)

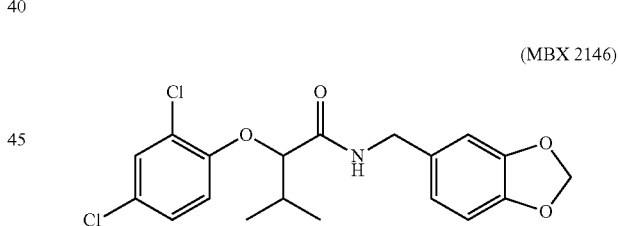

White beads; R$_f$ 0.80 (50% EtOAc/hexanes); m.p. 73-75° C.; $^1$H-NMR [300 MHz, CDCl3]: δ 7.36 (d, 1H), 7.15 (dd, 1H), 6.80 (d, 1H), 6.71 (d, 1H), 6.64-6.62 (m, 3H), 5.94 (s, 2H), 4.43 (d, 1H), 4.36-4.33 (m, 2H), 2.38-2.32 (m, 1H), 1.10 (s, 3H), 1.07 (s, 3H); LCMS: 396.1 (M+1).

(MBX 2263)

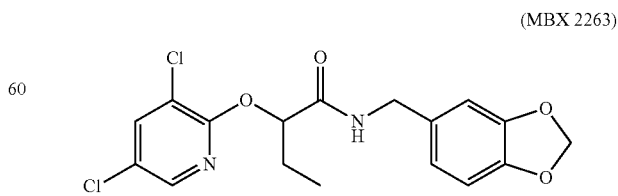

Light yellow beads; R$_f$ 0.71 (50% EtOAc/hexanes); m.p. 159-161° C.; $^1$H-NMR [300 MHz, CDCl$_3$]: δ 8.00 (d, 1H), 7.67 (d, 1H), 6.74-6.66 (m, 3H), 6.57 (br s, 1H), 5.94 (s, 2H), 5.45-5.42 (m, 1H), 4.38 (d, 2H), 2.12-2.02 (m, 1H), 1.01 (t, 3H); LCMS: 405.0 (M+Na).

(MBX 2084)

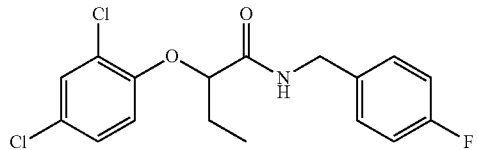

White crystals; R$_f$ 0.65 (50% EtOAc/hexanes); m.p. 108-109° C.; $^1$H-NMR [300 MHz, CDCl3]: δ 7.37 (d, 1H), 7.20-7.15 (m, 3H), 7.02-6.95 (m, 2H), 6.90 (br s, 1H), 6.82 (d, 1H), 4.62 (t, 1H), 4.51-4.34 (m, 2H), 2.08-1.99 (m, 2H), 1.04 (t, 3H); LCMS: 358.3 (M+1).

(MBX 2083)

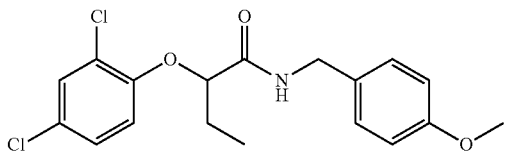

White beads; R$_f$ 0.66 (50% EtOAc/hexanes); m.p. 85-88° C.; $^1$H-NMR [300 MHz, CDCl3]: δ 7.36 (d, 1H), 7.18-7.10 (m, 3H), 6.85-6.81 (m, 4H), 4.61 (t, 1H), 4.47-4.34 (m, 2H), 3.79 (s, 3H), 2.08-1.99 (m, 2H), 1.04 (t, 3H); LCMS: 392.2 (M+Na).

(MBX 2088)

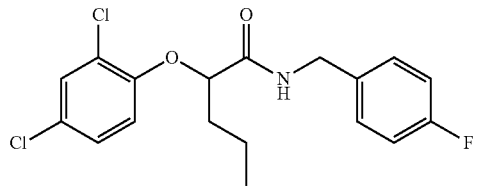

Yellowish white powder; R$_f$ 0.72 (50% EtOAc/hexanes); m.p. 119-121° C.; $^1$H-NMR [300 MHz, CDCl3]: δ 7.37 (d, 1H), 7.18-7.13 (m, 3H), 7.02-6.95 (m, 2H), 6.84-6.80 (m, 2H), 4.64 (t, 1H), 4.42 (d, 2H), 2.01-1.93 (m, 2H), 1.57-1.46 (m, 2H+H$_2$O), 0.95 (t, 3H); LCMS: 372.4 (M+1).

(MBX 2087)

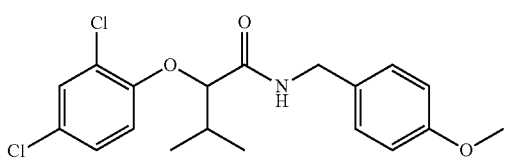

White/translucent flecks; R$_f$ 0.68 (50% EtOAc/hexanes); m.p. 103-104° C.; $^1$H-NMR [300 MHz, CDCl3]: δ 7.35 (d, 1H), 7.16 (dd, 1H), 7.10 (d, 2H), 6.85-6.80 (m, 3H), 6.76 (br s, 1H), 4.63 (t, 1H), 4.39 (d, 2H), 3.79 (s, 3H), 2.01-1.93 (m, 2H), 1.56-1.48 (m, 2H), 0.95 (t, 3H); LCMS: 406.4 (M+Na).

(MBX 2149)

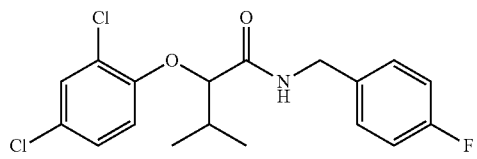

Peach colored crystals; R$_f$ 0.80 (50% EtOAc/hexanes); m.p. 143-146° C.; $^1$H-NMR [300 MHz, CDCl3]: δ 7.36 (d, 1H), 7.17-7.10 (m, 3H), 7.01-6.94 (m, 2H), 6.80 (d, 2H), 6.72 (br s, 1H), 4.49-4.34 (m, 3H), 2.39-2.31 (m, 1H), 1.09 (s, 3H), 1.07 (s, 3H); LCMS: 370.1 (M+1).

(MBX 2148)

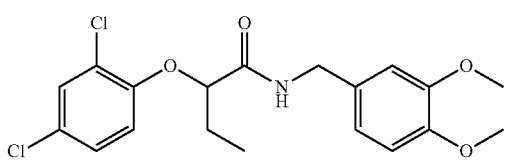

Off-white beads; R$_f$ 0.77 (50% EtOAc/hexanes); m.p. 76-79° C.; $^1$H-NMR [300 MHz, CDCl3]: δ 7.35 (d, 1H), 7.14 (dd, 1H), 7.09 (d, 1H), 6.82-6.78 (m, 3H), 6.63 (br s, 1H), 4.45-4.31 (m, 3H), 3.79 (s, 3H), 2.39-2.32 (m, 1H), 1.09 (s, 3H), 1.07 (s, 3H); LCMS: 382.3 (M+1).

(MBX 2264)

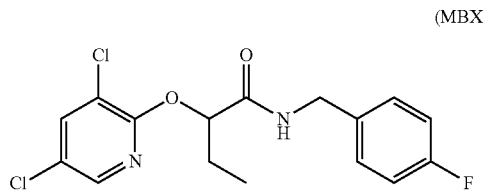

Off-white needle crystals; R$_f$ 0.72 (50% EtOAc/hexanes); m.p. 119-122° C.; $^1$H-NMR [300 MHz, CDCl3]: δ 7.99 (d, 1H), 7.68 (d, 1H), 7.21-7.17 (m, 2H), 7.03-6.95 (m, 2H), 6.65 (br s, 1H), 5.46 (t, 1H), 4.45 (d, 2H), 2.13-2.02 (m, 2H), 1.01 (t, 3H); LCMS: 379.0 (M+Na).

(MBX 2082)

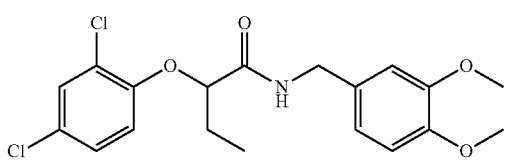

White powder; R$_f$ 0.49 (50% EtOAc/hexanes); m.p. 117-118° C.; $^1$H-NMR [300 MHz, CDCl3]: δ 7.37 (d, 1H), 7.16 (dd, 1H), 6.85-6.80 (m, 2H), 6.78-6.73 (m, 3H), 4.62 (t, 1H), 4.48-4.35 (m, 2H), 3.86 (s, 3H), 3.81 (s, 3H), 2.09-2.00 (m, 2H), 1.05 (t, 3H); LCMS: 422.2 (M+Na).

(MBX 2086)

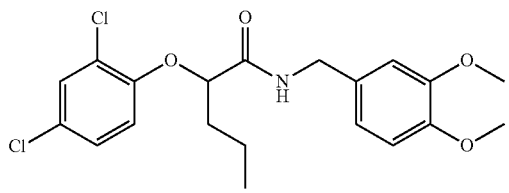

Off-white powder; $R_f$ 0.57 (50% EtOAc/hexanes); m.p. 81-83° C.; $^1$H-NMR [300 MHz, CDCl3]: δ 7.36 (d, 1H), 7.16 (dd, 1H), 6.84-6.71 (m, 5H), 4.64 (t, 1H) 4.40 (d, 2H), 3.86 (s, 3H), 3.80 (s, 3H), 2.02-1.94 (m, 2H), 1.57-1.49 (m, 2H+H$_2$O), 0.95 (t, 3H); LCMS: 436.2 (M+Na).

(MBX 2147)

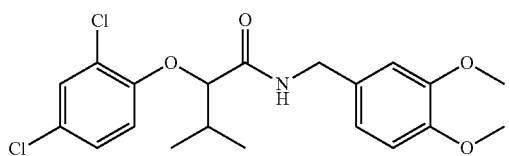

White powder; $R_f$ 0.70 (50% EtOAc/hexanes); m.p. 108-110° C.; $^1$H-NMR [300 MHz, CDCl3]: δ 7.36 (d, 1H), 7.15 (dd, 1H), 6.82-6.67 (m, 5H), 4.47-4.31 (m, 3H), 3.86 (s, 3H), 3.79 (s, 3H), 2.39-2.34 (m, 1H), 1.11 (s, 3H), 1.08 (s, 3H); LCMS: 412.0 (M+1).

(MBX 2159)

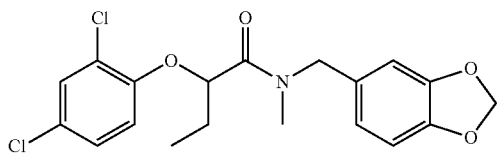

Light yellow sticky oil; $R_f$ 0.71 (50% EtOAc/hexanes); m.p. NA; $^1$H-NMR [300 MHz, CDCl3]: δ 7.36 (d, 0.7H), 7.30 (d, 0.3H), 7.13 (dd, 1H), 6.89-6.81 (m, 1H), 6.69 (d, 1H), 6.61-6.57 (m, 1.4H), 6.48-6.41 (m, 0.5H), 5.94 (br s, 2H), 4.78-4.73 (m, 1H), 4.64 (br s, 0.5H), 4.44 (br s, 1.4H), 2.98 (s, 2.1H), 2.85 (s, 0.8H), 2.10-2.00 (m, 2H), 1.17-1.10 (m, 3H); LCMS: 396.1 (M+1).

(MBX 2359)

Off-white needle crystals; $R_f$ 0.73 (50% EtAc/Hexanes); m.p. 125-127° C.; $^1$H-NMR [300 MHz, CDCl3]: δ 7.99 (d, 1H), 7.80 (d, 1H), 7.65 (d, 2H), 7.45 (d, 1H), 7.26 (d, 1H+CHCl$_3$), 7.20 (dd, 1H), 6.69 (br s, 1H), 5.47 (t, 1H), 4.60 (dd, 2H), 2.12-2.06 (m, 2H), 1.03 (t, 3H); LCMS: 394.8 (M+1).

In addition scheme 1 below provides a suitable synthesis scheme for the preferred embodiments, designated MBX-2359, MBX-2401, and MBX 2402, (i.e., the racemate, R-, and S-isomers, respectively, of N-(benzo[b]thiophen-5-ylmethyl)-2-(3,5-dichloropyridin-2-yloxy)butanamide.

Scheme 1

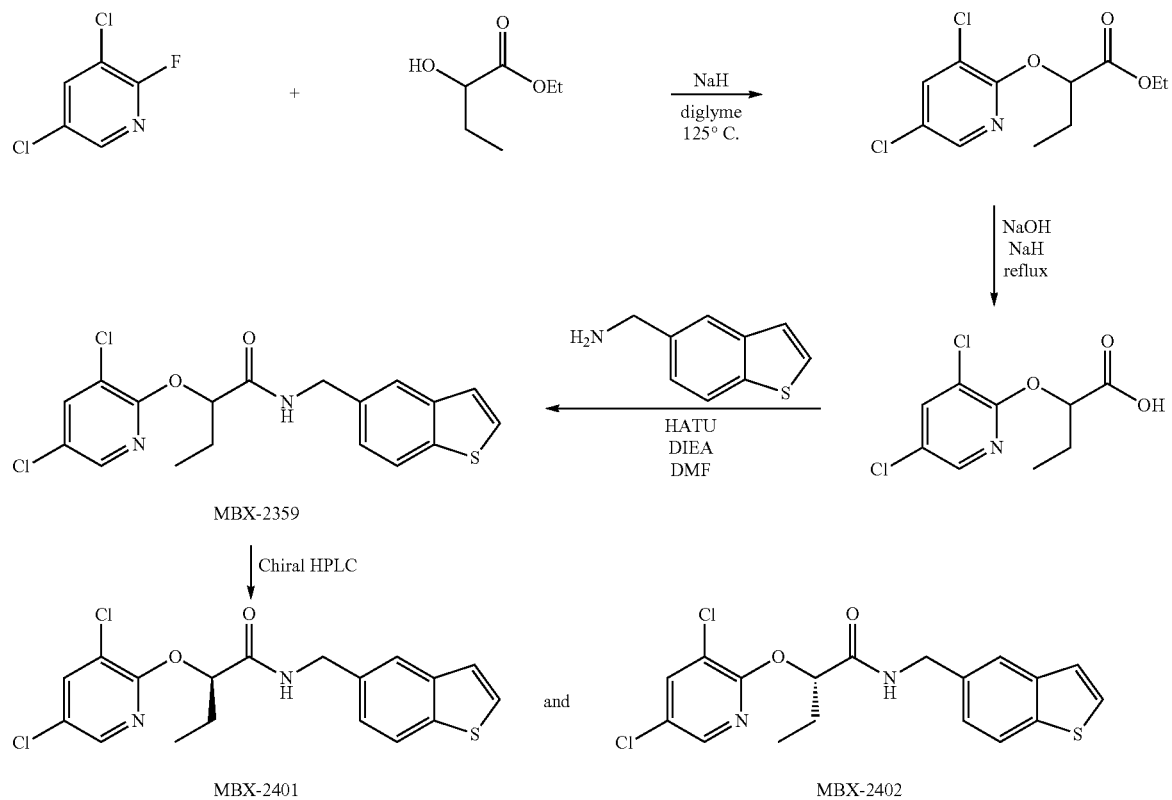

The synthesis begins with the base-promoted displacement of the 2-fluoro substituent of 3,5-dichloro-2-fluoropyridine with ethyl 2-hydroxybutanoate. Saponification of the resulting ester is then followed by peptide coupling using benzo[b]thiophene-5-ylmethanamine produces a racemic mixture of the target compound MBX-2359. Chiral HPLC is then used to separate the two enantiomers, MBX-2401 and MBX-2402 in their enantiomerically pure (e.g., >99%) forms.

The T3SS inhibitor compounds described herein are organic compounds that can also be synthesized to order by commercial suppliers such as ChemBridge Corporation (San Diego, Calif., USA), Life Chemicals Inc. (Burlington, ON, Canada), and Timtec LLC (Newark, Del., USA).

Unless otherwise indicated, it is understood that description of the use of a T3SS inhibitor compound in a composition or method also encompasses the embodiment wherein a combination of two or more T3SS inhibitor compounds are employed as the source of T3SS inhibitory activity in a composition or method of the invention.

Pharmaceutical compositions according to the invention comprise a T3SS inhibitor compound as described herein, or a pharmaceutically acceptable salt thereof, as the "active ingredient" and a pharmaceutically acceptable carrier (or "vehicle"), which may be a liquid, solid, or semi-solid compound. A "pharmaceutically acceptable" compound or composition means that the compound or composition is not biologically, chemically, or in any other way, incompatible with body chemistry and metabolism and also does not adversely affect the activity of the T3SS inhibitor or any other component that may be present in a composition in such a way that would compromise the desired therapeutic and/or preventative benefit to a patient. Pharmaceutically acceptable carriers useful in the invention include those that are known in the art of preparation of pharmaceutical compositions and include, without limitation, water, physiological pH buffers, physiologically compatible salt solutions (e.g., phosphate buffered saline), and isotonic solutions. Pharmaceutical compositions of the invention may also comprise one or more excipients, i.e., compounds or compositions that contribute or enhance a desirable property in a composition other than the active ingredient.

Various aspects of formulating pharmaceutical compositions, including examples of various excipients, dosages, dosage forms, modes of administration, and the like are known to those skilled in the art of pharmaceutical compositions and also available in standard pharmaceutical texts, such as *Remington's Pharmaceutical Sciences,* 18th edition, Alfonso R. Gennaro, ed. (Mack Publishing Co., Easton, Pa. 1990), *Remington: The Science and Practice of Pharmacy, Volumes* 1 & 2, 19th edition, Alfonso R. Gennaro, ed., (Mack Publishing Co., Easton, Pa. 1995), or other standard texts on preparation of pharmaceutical compositions.

Pharmaceutical compositions may be in any of a variety of dosage forms particularly suited for an intended mode of administration. Such dosage forms, include, but are not limited to, aqueous solutions, suspensions, syrups, elixirs, tablets, lozenges, pills, capsules, powders, films, suppositories, and powders, including inhalable formulations. Preferably, the pharmaceutical composition is in a unit dosage form suitable for single administration of a precise dosage, which may be a fraction or a multiple of a dose that is calculated to produce effective inhibition of T3 SS.

A composition comprising a T3SS inhibitor compound (or combination of T3SS inhibitors) described herein may optionally possess a second active ingredient (also referred to as "second agent", "second active agent") that provides one or more other desirable therapeutic or prophylactic activities other than T3SS inhibitory activity. Such a second agent useful in compositions of the invention includes, but is not limited to, an antibiotic, an antibody, an antiviral agent, an anticancer agent, an analgesic agent, a nonsteroidal anti-inflammatory drug (NSAID), acetaminophen, an opioid, a COX-2 inhibitor), an immunostimulatory agent (e.g., a cytokine or a synthetic immunostimulatory organic molecule), a hormone (natural, synthetic, or semisynthetic), a central nervous system (CNS) stimulant, an antiemetic agent, an antihistamine, an erythropoietin, a complement stimulating agent, a sedative, a muscle relaxant agent, an anesthetic agent, an anticonvulsive agent, an antidepressant, an antipsychotic agent, and combinations thereof.

Pharmaceutical compositions as described herein may be administered to humans and other animals in a manner similar to that used for other known therapeutic or prophylactic agents, and particularly as used for therapeutic aromatic or multi-ring antibiotics. The dosage to be administered to an individual and the mode of administration will depend on a variety of factors including age, weight, sex, condition of the patient, and genetic factors, and will ultimately be decided by an attending qualified healthcare provider.

Pharmaceutically acceptable salts of T3SS inhibitor compounds described herein include those derived from pharmaceutically acceptable inorganic and organic acids and bases. Examples of suitable acids include hydrochloric, hydrobromic, sulfuric, nitric, perchloric, fumaric, maleic, malic, pamoic, phosphoric, glycolic, lactic, salicylic, succinic, toluene-p-sulfonic, tartaric, acetic, citric, methanesulfonic, formic, benzoic, malonic, naphthalene-2-sulfonic, tannic, carboxymethyl cellulose, polylactic, polyglycolic, and benzenesulfonic acids.

The invention may also envision the "quaternization" of any basic nitrogen-containing groups of a compound described herein, provided such quaternization does not destroy the ability of the compound to inhibit T3SS. Such quaternization may be especially desirable to enhance solubility. Any basic nitrogen can be quaternized with any of a variety of compounds, including but not limited to, lower (e.g., $C_1$-$C_4$) alkyl halides (e.g., methyl, ethyl, propyl and butyl chlorides, bromides, and iodides); dialkyl sulfates (e.g., dimethyl, diethyl, dibutyl and diamyl sulfates); long chain halides (e.g., decyl, lauryl myristyl and stearyl chlorides, bromides and iodides); and aralkyl halides (e.g., benzyl and phenethyl bromides).

For solid compositions, conventional nontoxic solid carriers may be used including, but not limited to, mannitol, lactose, starch, magnesium stearate, sodium saccharin, talc, cellulose, glucose, sucrose, and magnesium carbonate.

Pharmaceutical compositions may be formulated for administration to a patient by any of a variety of parenteral and non-parenteral routes or modes. Such routes include, without limitation, intravenous, intramuscular, intra-articular, intraperitoneal, intracranial, paravertebral, periarticular, periostal, subcutaneous, intracutaneous, intrasynovial, intrasternal, intrathecal, intralesional, intratracheal, sublingual, pulmonary, topical, rectal, nasal, buccal, vaginal, or via an implanted reservoir. Implanted reservoirs may function by mechanical, osmotic, or other means. Generally and particularly when administration is via an intravenous, intra-arterial, or intramuscular route, a pharmaceutical composition may be given as a bolus, as two or more doses separated in time, or as a constant or non-linear flow infusion.

A pharmaceutical composition may be in the form of a sterile injectable preparation, e.g., as a sterile injectable aqueous solution or an oleaginous suspension. Such preparations may be formulated according to techniques known in the art using suitable dispersing or wetting agents (e.g., polyoxyethylene 20 sorbitan monooleate (also referred to as "polysorbate 80"); TWEEN® 80, ICI Americas, Inc., Bridgewater, N.J.) and suspending agents. Among the acceptable vehicles and solvents that may be employed for injectable formulations are mannitol, water, Ringer's solution, isotonic sodium chloride solution, and a 1,3-butanediol solution. In addition, sterile, fixed oils may be conventionally employed as a solvent or suspending medium. For this purpose, a bland fixed oil may be employed including synthetic mono- or diglycerides. Fatty acids, such as oleic acid and its glyceride derivatives are useful in the preparation of injectables, as are natural pharmaceutically-acceptable oils, including olive oil or castor oil, especially in their polyoxyethylated versions.

A T3SS inhibitor described herein may be formulated in any of a variety of orally administrable dosage forms including, but not limited to, capsules, tablets, caplets, pills, films, aqueous solutions, oleaginous suspensions, syrups, or elixirs. In the case of tablets for oral use, carriers, which are commonly used include lactose and corn starch. Lubricating agents, such as magnesium stearate, are also typically added. For oral administration in a capsule form, useful diluents include lactose and dried cornstarch. Capsules, tablets, pills, films, lozenges, and caplets may be formulated for delayed or sustained release.

Tablets and other solid or semi-solid formulations may be prepared that rapidly disintegrate or dissolve in an individual's mouth. Such rapid disintegration or rapid dissolving formulations may eliminate or greatly reduce the use of exogenous water as a swallowing aid. Furthermore, rapid disintegration or rapid dissolve formulations are also particularly useful in treating individuals with swallowing difficulties. For such formulations, a small volume of saliva is usually sufficient to result in tablet disintegration in the oral cavity. The active ingredient (a T3SS inhibitor described herein) can then be absorbed partially or entirely into the circulation from blood vessels underlying the oral mucosa (e.g., sublingual and/or buccal mucosa), or it can be swallowed as a solution to be absorbed from the gastrointestinal tract.

When aqueous suspensions are to be administered orally, whether for absorption by the oral mucosa or absorption via the gut (stomach and intestines), a composition comprising a T3SS inhibitor may be advantageously combined with emulsifying and/or suspending agents. Such compositions may be in the form of a liquid, dissolvable film, dissolvable solid (e.g., lozenge), or semi-solid (chewable and digestible). If desired, such orally administrable compositions may also contain one or more other excipients, such as a sweetener, a flavoring agent, a taste-masking agent, a coloring agent, and combinations thereof.

The pharmaceutical compositions comprising a T3SS inhibitor as described herein may also be formulated as suppositories for vaginal or rectal administration. Such compositions can be prepared by mixing a T3SS inhibitor compound as described herein with a suitable, non-irritating excipient that is solid at room temperature but liquid at body temperature and, therefore, will melt in the appropriate body space to release the T3SS inhibitor and any other desired component of the composition. Excipients that are particularly useful in such compositions include, but are not limited to, cocoa butter, beeswax, and polyethylene glycols.

Topical administration of a T3SS inhibitor may be useful when the desired treatment involves areas or organs accessible by topical application, such as the epidermis, surface wounds, or areas made accessible during surgery. Carriers for topical administration of a T3SS inhibitor described herein include, but are not limited to, mineral oil, liquid petroleum, white petroleum, propylene glycol, polyoxyethylene polyoxypropylene compounds, emulsifying wax, and water. Alternatively, a topical composition comprising a T3SS inhibitor as described herein may be formulated with a suitable lotion or cream that contains the inhibitor suspended or dissolved in a suitable carrier to promote absorption of the inhibitor by the upper dermal layers without significant penetration to the lower dermal layers and underlying vasculature. Carriers that are particularly suited for topical administration include, but are not limited to, mineral oil, sorbitan monostearate, polysorbate 60, cetyl esters wax, cetearyl alcohol, 2-octyldodecanol, benzyl alcohol, and water. A T3SS inhibitor may also be formulated for topical application as a jelly, gel, or emollient. Topical administration may also be accomplished via a dermal patch.

Persons skilled in the field of topical and transdermal formulations are aware that selection and formulation of various ingredients, such as absorption enhancers, emollients, and other agents, can provide a composition that is particularly suited for topical administration (i.e., staying predominantly on the surface or upper dermal layers with minimal or no absorption by lower dermal layers and underlying vasculature) or transdermal administration (absorption across the upper dermal layers and penetrating to the lower dermal layers and underlying vasculature).

Pharmaceutical compositions comprising a T3SS inhibitor as described herein may be formulated for nasal administrations, in which case absorption may occur via the mucous membranes of the nasal passages or the lungs. Such modes of administration typically require that the composition be provided in the form of a powder, solution, or liquid suspension, which is then mixed with a gas (e.g., air, oxygen, nitrogen, or a combination thereof) so as to generate an aerosol or suspension of droplets or panicles. Inhalable powder compositions preferably employ a low or non-irritating powder carrier, such as melezitose (melicitose). Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. A pharmaceutical composition comprising a T3SS inhibitor described herein for administration via the nasal passages or lungs may be particularly effective in treating lung infections, such as hospital-acquired pneumonia (HAP).

Pharmaceutical compositions described herein may be packaged in a variety of ways appropriate to the dosage form and mode of administration. These include but are not limited to vials, bottles, cans, packets, ampoules, cartons, flexible containers, inhalers, and nebulizers. Such compositions may be packaged for single or multiple administrations from the same container. Kits may be provided comprising a composition, preferably as a dry powder or lyophilized form, comprising a T3SS inhibitor and preferably an appropriate diluent, which is combined with the dry or lyophilized composition shortly before administration as explained in the accompanying instructions of use. Pharmaceutical composition may also be packaged in single use pre-filled syringes or in cartridges for auto-injectors and needleless jet injectors. Multi-use packaging may require the addition of antimicrobial agents such as phenol, benzyl alcohol, meta-cresol, methyl paraben, propyl paraben, benzalconium chloride, and benzethonium chloride, at concentrations that will prevent the growth of bacteria, fungi, and the like, but that are non-toxic when administered to a patient.

Consistent with good manufacturing practices, which are in current use in the pharmaceutical industry and which are well known to the skilled practitioner, all components contacting or comprising a pharmaceutical composition must be sterile and periodically tested for sterility in accordance with industry norms. Methods for sterilization include ultrafiltration, autoclaving, dry and wet heating, exposure to gases such as ethylene oxide, exposure to liquids, such as oxidizing agents, including sodium hypochlorite (bleach), exposure to high energy electromagnetic radiation (e.g., ultraviolet light, x-rays, gamma rays, ionizing radiation). Choice of method of sterilization will be made by the skilled practitioner with the goal of effecting the most efficient sterilization that does not significantly alter a desired biological function of the T3SS inhibitor or other component of the composition.

Additional embodiments and features of the invention will be apparent from the following non-limiting examples.

Example 1

Materials and Methods for Characterization of T3SS Inhibitors

Strains, Plasmids, and Growth Media.
Bacterial strains and plasmids used for assays are described in Table 1, below. All *P. aeruginosa* strains were derivatives of PAO1 (Holloway, et al., 1979, *Microbiol. Rev.*, 43:73-102), PAK (Bradley, D. E., 1974, *Virology*, 58:149-63), or PA14 (Rahme, et al., 1995, *Science*, 268:1899-902). *E. coli* TOP 10 (Invitrogen), *E. coli* DB3.1 GATEWAY® host, Invitrogen), *E. coli* SM10 (de Lorenzo and Timmis, 1994, *Methods Enzymol.*, 235:386-405), and *E. coli* S17-1 (ATCC 47055) were used as hosts for molecular cloning. Luria-Bertani (LB) medium (liquid and agar) was purchased from Difco. LB was supplemented with 30 μg/ml gentamicin (LBG) with or without 1 mM isopropyl-β-D-thiogalactopyranoside (IPTG) and 5 mM EGTA (LBGI and LBGIE, respectively).

TABLE 1

Strains and Plasmids

| Strain | Genotype/Features | Reference or Source |
|---|---|---|
| *P. aeruginosa*: | | |
| MDM852 | PA01::pGSV3-'exoT'-luxCDABE | (1) |
| MDM1355 | PA01 ΔpscC::pGSV3-'exoT'-luxCDABE | (1) |

TABLE 1-continued

Strains and Plasmids

| Strain | Genotype/Features | Reference or Source |
|---|---|---|
| MDM973 | PAK/pUCP24GW-lacI$^Q$-lacPO-exoS::blaM | (1) |
| MDM974 | PAK ΔpscC/pUCP24GW-lacI$^Q$-lacPO-exoS::blaM | (1) |
| MDM1156 | PAO-LAC/pUCP24GW-lacPO-luxCDABE | (1) |
| PAKΔC | PAK ΔpscC; T3SS defective | (2) |
| PAKΔS | PAK ΔexoS; secretes ExoT as its only cytotoxic T3SS effector | (2) |
| PAKΔSTYexoU | PAK ΔexoS::miniCTX-exoU-spcU; secretes ExoU as its only cytotoxic T3SS effector | (2) |
| PAKΔTY | PAK ΔexoT ΔexoY; secretes ExoS as its only T3SS effector | (2) |
| MDM1387 | PA14 xcpQ::MrT7; (aka, PAMr_nr_mas_02_2:H7) defective in type II secretion | (3) |
| *Y. pestis*: | | |
| JG153/pMM85 | KIM Δpgm pPCP1⁻ pCD1⁺/pHSG576 yopE::blaM | (4, 5) |

(1) Aiello, et al., 2010, *Antimicrob. Agents Chemother.*, 54: 1988-99.
(2) Lee, et al., 2005, *Infect. Immun.*, 73: 1695-705.
(3) Liberati, et al., *Proc. Natl. Acad. Sci. USA*, 103: 2833-8.
(4) Marketon, et al., 2005, *Science*, 309: 1739-41.
(5) Pan, et al., 2009, *Antimicrob. Agents Chemother.*, 53: 385-92.
The *Y. pestis* reporter strain was kindly provided by Dr. Jon Gaguen (U. Massachusetts Medical School).
Plasmid pGSV3-Lux was kindly provided by Dr. Donald Woods (U. Calgary).

PCR and Primers.

Synthetic oligonucleotide primers (from Eurofins MWG Operon; Huntsville, Ala., USA) were designed using the published genome sequence for *P. aeruginosa* (Stover, et al., 2000, *Nature*, 406:959-64) and web-based PRIMER3 (Whitehead Institute). Primers were used at 10 μM in PCR amplifications with FAILSAFE® polymerase (Epicentre), Buffer G (Epicentre), and 4% DMSO for *P. aeruginosa* chromosomal DNA templates.

TABLE 2

Primers Used

| # | Primer Name | Primer Sequence |
|---|---|---|
| 1 | exoT-F + EcoRI | TACTACGAATTCCCAGGAAGCACCGAAGG (SEQ ID NO: 1) |
| 2 | exoT-R + EcoRI | CATTACGAATTCCTGGTACTCGCCGTTGGTAT (SEQ ID NO: 2) |
| 3 | exoT-out-F | TAGGGAAAGTCCGCTGTTTT (SEQ ID NO: 3) |
| 4 | luxC-R | CCTGAGGTAGCCATTCATCC (SEQ ID NO: 4) |
| 5 | exoS-F + GWL | TACAAAAAAGCAGGCTAGGAAACAGACATGCATATTCAATCGCTTCAG (SEQ ID NO: 5) |
| 6 | exoS(234)-R | ATCTTTTACTTTCACCAGCGTTTCTGGGTGACCGTCGGCCGATACTCTGCT (SEQ ID NO: 6) |
| 7 | BLA-F | CACCCAGAAACGCTGGTGAA (SEQ ID NO: 7) |
| 8 | BLA-R + GWR | TACAAGAAAGCTGGGTTTGGTCTGACAGTTACCAATGC (SEQ ID NO: 8) |
| 9 | GW-attB1 | GGGGACAAGTTTGTACAAAAAAGCAGGCT (SEQ ID NO: 9) |

TABLE 2-continued

Primers Used

| # | Primer Name | Primer Sequence |
|---|---|---|
| 10 | GW-attB2 | GGGGACCACTTTGTACAAGAAAGCTGGGT (SEQ ID NO: 10) |
| 11 | lux-F + GWL | TACAAAAAAGCAGGCTAGGAAACAGCTATGACGAAGAAG ATCAGTTTTATAATTAACGGCCAGGTTGAAATC (SEQ ID NO: 11) |
| 12 | lux-R + GWR | TACAAGAAAGCTGGGTGTTTTCCCAGTCACGACGTT (SEQ ID NO: 12) |

Luciferase Transcriptional Reporter Screen.

A transcriptional fusion of the *Photorhabdus luminescens* lux operon (luxCDABE) to effector gene exoT (PA0044) was constructed by inserting an internal fragment of the exoT gene (712 bp generated by PCR with primers exoT-F+EcoRI/exoT-R+EcoRI, Table 2, above) into EcoRI-cut reporter plasmid pGSV3-lux-Gm (Moore, et al., 2004, *Infect. Immun.*, 72:4172-87 as described in Moir, et al., 2008, *Trans. R. Soc. Trop. Med. Hyg.*, 102 Suppl 1:S152-62. The resulting plasmid was introduced into *E. coli* SM10 cells and transferred into *P. aeruginosa* PAO1 and PA01 ΔpscC cells by conjugation to generate recombinant reporter strains MDM852 and MDM1355, respectively. Insertion at the exoT chromosomal locus was confirmed by PCR with a primer outside of the cloned locus (exoT-out-F) and a primer within the luxC gene (luxC-R) (Table 2, above).

For inhibitor testing, compound master plates were thawed at room temperature on the day of the test, and 1 µl of compound (final 45 µM compound and 1.8% DMSO) was added to the 384-well opaque black screening plates using a Sciclone ALH 3000 liquid handling robot (Caliper, Inc.) and a Twister II Microplate Handler (Caliper, Inc.). Reporter strain MDM852 was grown at 37° C. in LBGI to $OD_{600}$~0.025-0.05, transferred into microplates (50 µl/well) containing test compounds and EGTA (5 µl of 0.1 M stock solution), which were covered with a translucent gas-permeable seal (Abgene, Inc., Cat. No. AB-0718). Control wells contained cells with fully induced T3SS (EGTA and DMSO, columns 1 and 2) and uninduced T3SS (DMSO only, columns 23 and 24). Plates were incubated at room temperature for 300 min. Then, luminescence was measured in an Envision Multilabel microplate reader (PerkinElmer). The screening window coefficient, Z'-factor (see Zhang, et al., 1999, *J. Biomol. Screen.*, 4:67-73), defined as the ratio of the positive and negative control separation band to the signal dynamic range of the assay, averaged 0.7 for the screen. All screening data, including the z-score, and confirmation and validation data were stored in one central database (CambridgeSoft's ChemOffice 11.0). Compounds were confirmed to be >95% pure and to be of the expected mass by LCMS analysis.

Effector-β-Lactamase (βLA) Secretion Assays.

(a) *P. aeruginosa*. A gene encoding an ExoS'-β-lactamase (βLA) fusion protein (comprised of 234 codons of *P. aeruginosa* effector ExoS fused to the TEM-1 β-lactamase gene lacking secretion signal codons) was constructed by splicing by overlap extension PCR(SOE-PCR) (Choi and Schweizer, 2005, *BMC Microbiol.*, 5:30) using primers 5-10 (Table 2, above), sequence confirmed, cloned into lacI$^Q$-containing GATEWAY® vector pUCP24GW (see Moir, et al., 2007, *J. Biomol. Screen.*, 12:855-64) behind the lac promoter, and introduced into *P. aeruginosa* by electroporation (see Choi, et al., 2006, *J. Microbial. Methods*, 64:391-7). Secretion of fusion proteins was detected by measuring the hydrolysis of the chromogenic β-lactamase substrate nitrocefin in clear 96-well microplates in a modification of a previously described assay (Lee, et al., 2007, *Infect. Immun.*, 75:1089-98). Cells of strain MDM973 (PAK/pUCP24GW-exoS::blaM) were sub-cultured in the morning from overnight growths in LBG into 0.1 ml of LBGIE with or without test compounds and grown for 150 min. Nitrocefin (100 µg/ml final) was added, and $A_{490}$ measurements taken every minute for 15 min in a Victor$^3$V 1420 Multilabel HTS Counter (PerkinElmer). Slopes were calculated as a relative measure of the quantity of the effector-βLA fusion protein secreted and were absolutely dependent on induction with IPTG, EGTA, and the presence of a functional pscC gene in the *P. aeruginosa* cells. Typical signal:background ratios were 6-10.

(b) *Yersinia pestis*. Attenuated *Y. pestis* strain JG 153 (gift of Jon Goguen, U. of Massachusetts Medical School, Worcester, Mass.) carrying plasmid pMM85 (yopE::blaM) was grown in LB+20 µg/ml chloramphenicol at 30° C. to prevent T3SS induction and loss of the pCD1 plasmid encoding T3SS. To induce T3SS, cells were shifted from 30° C. to 37° C. and EGTA was added to 1 mM final concentration. Cell culture (0.1 ml) was added to clear 96-well microplates containing test compound and incubated for 3 hours at 37° C. Nitrocefin was added (100 µg/ml final), and $A_{490}$ measurements were taken every minute for 10 minutes in an Envision Multilabel microplate reader (PerkinElmer). Slopes were plotted vs. the inhibitor concentration to determine $IC_{50}$ values.

Assay for Inhibition of Bioluminescence of Lac-promoted luxCDABE.

The complete *Photorhabdus luminescens* luxCDABE locus was amplified from pGSV3-lux (Moore, et al., 2004, *Infect. Immun.*, 72:4172-87) by PCR with Phusion polymerase (NEB, Beverly, Mass.) and primers lux-F+GWL and lux-R+GWR, followed by a second PCR with primers GW-attB1 and GW-attB2 to provide the full Gateway recognition sequence (Table 2). The ~5.8 kb product was gel-purified and inserted into pDONR221 with BPClonase® enzyme (Invitrogen, Inc.), and then into pUCP24GW (Moir, et al., 2007, *J. Biomol. Screen.*, 12:855-64) with LRClonase® enzyme (Invitrogen, Inc.). The resulting pUCP24GW-lacPO-luxCDABE plasmid was introduced into the *P. aeruginosa* PAO-LAC strain carrying one chromosomal copy of the lac repressor, lacI$^Q$, at the phiCTX locus (Hoang, et al., 2000, *Plasmid*, 43:59-72) by electroporation, selecting for gentamicin-resistance (Choi, et al., 2006, *J. Microbiol. Methods*, 64:391-7). To measure the effects of T3SS inhibitors on lac-promoted luciferase production, the resulting strain MDM1156 was subcultured from overnight LBG growths into LBGI at an $A_{600}$~0.05 and grown for 3 h in the presence or absence of inhibitors at 50 μM. The percent inhibition by compounds of RLU produced by lac-promoted vs. exoT-promoted luciferase was calculated and used as an indication of the T3 SS-selectivity.

Detection of Inhibition of T3SS-mediated ExoS Secretion into Culture Broths

*P. aeruginosa* strain PAKΔTY, which produces the ExoS, but not the ExoT or ExoY T3SS effectors, was grown overnight in LB and treated essentially as described previously (Lee, et al., 2005, *Infect. Immun.*, 73:1695-705). Bacteria were subcultured 1:1000 in LB supplemented with 5 mM EGTA and grown for 3 h at 37° C. with aeration in the presence or absence of inhibitors at the indicated concentrations. Bacteria were sedimented by centrifugation at 3,220×g for 15 min at 4° C. Culture supernatant was collected, and proteins were concentrated either by precipitation with 12.5% trichloroacetic acid followed by washing with acetone or by ultrafiltration. Proteins were resuspended according to original culture density ($A_{600}$), separated by sodium dodecyl sulfate-polyacrylamide gel electrophoresis (12.5% SDS-PAGE), and stained with Coomassie blue. Stained gel image files were processed with ImageJ software (ver. 1.42q, NIH) by subtracting the background, inverting the image, and integrating the density of each band.

Inhibition of *P. Aeruginosa* ExoU-dependent CHO Cell Killing.

Rescue of CHO cells from T3SS-mediated cytotoxicity of translocated effector protein ExoU was measured using a lactate dehydrogenase (LDH) release assay as previously reported (Lee, et al., 2005, *Infect. Immun.*, 73:1695-705) except that infection with *P. aeruginosa* was carried out for 2 hr in the absence of gentamicin. Percent cytotoxicity (% LDH release) was calculated relative to that of the uninfected control, which was set at 0% LDH release, and that of cells infected with *P. aeruginosa* unprotected by test compound (100% LDH release). LDH released from unprotected, infected cells reached at least 80% of the value obtained from complete lysis with 1% Triton X-100 in the 2 hr timeframe of this experiment. Pseudolipasin, which acts by direct inhibition of the ExoU phospholipase, was used as control inhibitor (Lee, et al, 2007, *Infect. Immun.*, 75:1089-98).

Gentamicin Protection Assays of Bacterial Internalization.

This assay was a modification of a previously published method of Ha and Jin, 2001, *Infect. Immun.*, 69:4398-406). A total of $2 \times 10^5$ HeLa cells were seeded into each well of a 12-well plate containing 2 ml per well of MEM supplemented with 10% FCS and incubated at 37° C. in 5% of $CO_2$ for 24 hr. After two washes with PBS, 1 ml of MEM containing 1% FCS was added to the HeLa cells. Test compound was added to half the wells at 50 μM final concentration (DMSO at 0.2% final). *P. aeruginosa* strains PAKΔC (negative control) and PAKΔS (positive control) were grown overnight in LB medium at 37° C. with shaking, diluted 1:1,000 in the morning and grown to an $OD_{600}$ of 0.3 (~$10^8$ cells/ml). Bacteria were washed in PBS, resuspended in 1 ml of MEM, and added to the HeLa cells at an MOI of 10 in the presence or absence of the test compound. Infected HeLa cells were incubated at 37° C. in 5% $CO_2$ for 2 h. After two washes with PBS, 1 ml of MEM containing 50 μg/ml gentamicin was added, and cells were incubated for an additional 2 hr. After three washes with PBS, the cells were lysed in PBS containing 0.25% Triton X-100, and dilutions were plated on LB-agar plates to count the number of bacteria internalized within HeLa cells.

Elastase Secretion Assay.

The effect of test compounds on type II-mediated secretion of elastase from *P. aeruginosa* was determined by a modification of a previously described method (Ohman, et al., 1980, *J. Bacteriol.*, 142:836-42. *P. aeruginosa* PA14 cells were cultured from a starting density of $A_{600}$~0.05 for 16 hr to saturation in LB in the presence or absence of test compound at 50 μM. Cells were removed by centrifugation in a microfuge, and 0.2 ml of cleared supernatant was added to 0.4 ml of a suspension of elastin-Congo Red (5 mg/ml, Sigma) in buffer consisting of 0.1 M Tris-HCl, pH 7.4 and 1 mM $CaCl_2$ in capped microfuge tubes. Tubes were incubated at 37° C. with shaking for 6 hr. Then, 0.4 nil of buffer consisting of 0.7 M sodium phosphate (pH 6.0) was added, tubes were centrifuged in a microfuge to remove undigested elastin-Congo Red, and $A_{495}$ of the cleared supernatants was measured. Readings were normalized to the original cell density ($OD_{600}$), and % inhibition of elastase secretion was determined relative to untreated PA14 (no inhibition control) and to untreated type II secretion defective PA14 xcpQ::MrT7 (Liberati, et al., *Proc. Natl. Acad. Sci. USA*, 103:2833-8, strain MDM1387, Table 1) (complete inhibition control).

*Chlamydia Trachomatis* Growth Inhibition Assay.

Inhibition of the growth of *Chlamydia trachomatis* L2 strain by compounds was measured in 24-well plates essentially according to the method of Wolf, et al., 2006, *Mol. Microbiol.*, 61:1543-55. Confluent monolayer Hep-2 cells were infected with L2 at an MOI of 0.5 and treated with compounds at indicated concentrations for 48 hr. Then cultures were collected and sonicated. Entire lysates were used for counting inclusion forming units (IFUs) as a measurement of production of *Chlamydia* progeny elementary bodies (EBs) by re-plating onto fresh HeLa monolayers. An uninhibited control (DMSO only) and a complete inhibition control (chloramphenicol, 200 μg/ml) were included. Experiments were done in triplicate.

Minimum Inhibitory Concentration (MIC).

MIC determination was done by the broth microdilution method described in the CLSI (formerly NCCLS) guidelines and expressed in μM to facilitate comparisons with $IC_{50}$ and $CC_{50}$ values. See, NCCLS, Approved standard M7-A4: Methods for dilution antimicrobial susceptibility tests for bacteria that grow aerobically, 4th ed. National Committee for Clinical Laboratory Standards, Wayne, Pa. (1997).

Determination of Mammalian Cytotoxicity.

The cytotoxic concentration ($CC_{50}$) of compound versus cultured mammalian cells (HeLa, ATCC CCL-2; American Type Culture Collection, Manassas, Va.) was determined as the concentration of compound that inhibits 50% of the conversion of MTS to formazan. See, Marshall, et al., 1995, A critical assessment of the use of microculture tetrazolium assays to measure cell growth and function, *Growth Regul.*, 5:69-84. Briefly, 96-well plates were seeded with HeLa cells at a density of $4 \times 10^3$ per well in VP-SFM medium without serum (Frazzati-Gallina, et al., 2001, *J. Biotechnol.*, 92:67-72), in the presence or absence of serial dilutions of a compound dissolved in DMSO. Following incubation for 3 days at 37° C. in VP-SFM, cell viability was measured with the vital tetrazolium salt stain 3-(4,5-dimethylthiazol-2-yl)-2,5 diphenyltetrazolium bromide according to the manufacturer's instructions (Promega, Madison, Wis.). Values were determined in duplicate using dilutions of inhibitory compound from 100 μM to 0.2 μM.

Example 2

Optimization of Alkyl Substituent at the Asymmetric Center

Several analogs of compound MBX-1641 were synthesized and their level of inhibition of T3SS-mediated secretion, translocation, and cytotoxicity determined. The results are set forth in Table 3.

TABLE 3

| MBX Cmpd. | Structure | Secretion IC$_{50}$ (μM)[1] | Translocation IC$_{50}$ (μM)[2] | CC$_{50}$ (μM)[3] | SI[4] |
|---|---|---|---|---|---|
| 1641 | (2,4-dichlorophenoxy)-methyl-acetamide-N-benzodioxole | 12.5 | 15 | 100 | 8 |
| 2081 | (2,4-dichlorophenoxy)-ethyl-acetamide-N-benzodioxole | 3.9 | 4.2 | >200 | >50 |
| 2085 | (2,4-dichlorophenoxy)-propyl-acetamide-N-benzodioxole | 14% @50 μM | n.d. | n.d. | — |
| 2146 | (2,4-dichlorophenoxy)-isopropyl-acetamide-N-benzodioxole | 100 | n.d. | n.d. | — | n.d. = not determined
[1] Concentration of half-maximal inhibition of T3SS-mediated secretion (ExoS'-βLA fusion protein assay)
[2] Concentration of half-maximal inhibition of T3SS-mediated translocation (ExoU intoxication of CHO cells)
[3] Concentration of half-maximal inhibition of HeLa cell cytotoxicity in serum-free media
[4] Selectivity Index (CC$_{50}$/secretion IC$_{50}$)

These preliminary studies confirmed that alteration of the methyl acetamide structure at any point of the structure had the ability to drastically change the T3SS inhibitory performance of the compounds, particularly substitution at the α carbon, where alteration of methyl to ethyl led to a over a 3-fold increase in the potency of inhibition of both T3SS-mediated secretion and T3SS-mediated translocation. See, FIG. 1.

Additional analogs were synthesized and tested. The results are set forth in Table 4. Values reflect 1-20 separate determinations; average values are presented where more than one determination was made.

TABLE 4

| MBX Cmpd. | Structure | Ave. Secretion IC$_{50}$ (μM) | Ave. Translocation IC$_{50}$ (μM)[1] | Ave. CC$_{50}$ (μM) | melting point (° C.) |
|---|---|---|---|---|---|
| 1641 | (2,4-dichlorophenoxy)-methyl-acetamide-N-benzodioxole | 7.0 | 11.2 | >100 | 120 |
| 2081 | (2,4-dichlorophenoxy)-ethyl-acetamide-N-benzodioxole | 3.9 | 4.2 | >200 | 112 |

TABLE 4-continued

| MBX Cmpd. | Structure | Ave. Secretion IC$_{50}$ (μM) | Ave. Translocation IC$_{50}$ (μM)[1] | Ave. CC$_{50}$ (μM) | melting point (°C.) |
|---|---|---|---|---|---|
| 2085 | 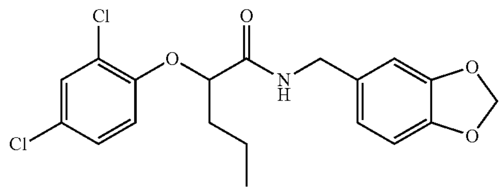 [SMILES: CCCC(Oc1ccc(Cl)cc1Cl)C(=O)NCc1ccc2c(c1)OCO2] | 14% @50 μM | n.d. | n.d. | 92 |
| 2146 | 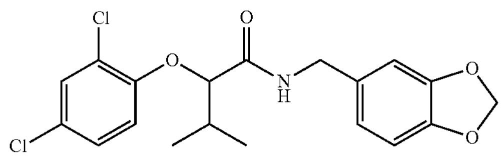 [SMILES: CC(C)C(Oc1ccc(Cl)cc1Cl)C(=O)NCc1ccc2c(c1)OCO2] | 100 | n.d. | n.d. | 74 |
| 2263 | 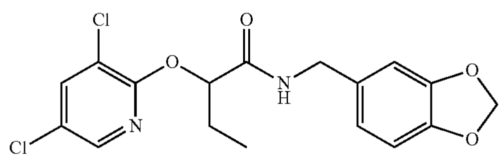 [SMILES: CCC(Oc1ncc(Cl)cc1Cl)C(=O)NCc1ccc2c(c1)OCO2] | 2 | 17 | >100 | 160 |
| 1642 | 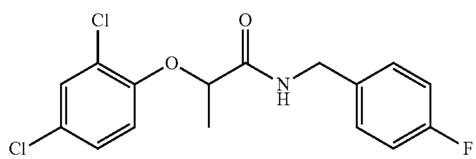 [SMILES: CC(Oc1ccc(Cl)cc1Cl)C(=O)NCc1ccc(F)cc1] | 9.8 | 15 | 41 | 110 |
| 2084 | 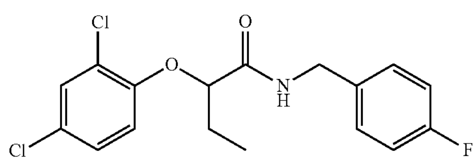 [SMILES: CCC(Oc1ccc(Cl)cc1Cl)C(=O)NCc1ccc(F)cc1] | 4.3 | 7.4 | 45 | 108 |
| 2088 | 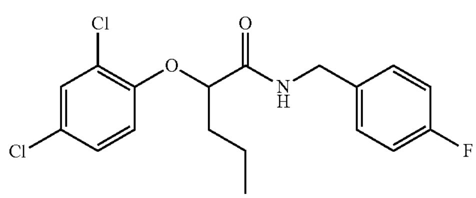 [SMILES: CCCC(Oc1ccc(Cl)cc1Cl)C(=O)NCc1ccc(F)cc1] | 9% @50 μM | n.d. | n.d. | 1120 |
| 2149 | 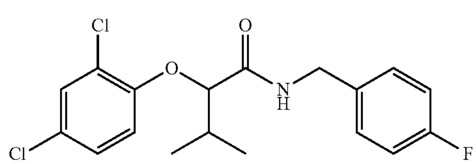 [SMILES: CC(C)C(Oc1ccc(Cl)cc1Cl)C(=O)NCc1ccc(F)cc1] | 1582.5 | n.d. | n.d. | 106 |
| 2264 | 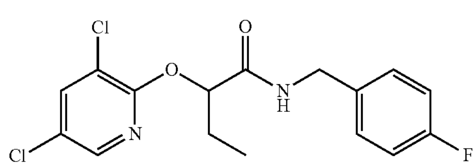 [SMILES: CCC(Oc1ncc(Cl)cc1Cl)C(=O)NCc1ccc(F)cc1] | 2 | 30 | 85 | 120 |
| 1940 | 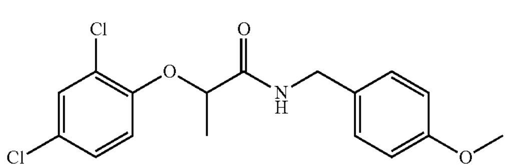 [SMILES: COc1ccc(CNC(=O)C(C)Oc2ccc(Cl)cc2Cl)cc1] | 12.4 | 22.5 | n.d. | 77 |

TABLE 4-continued

| MBX Cmpd. | Structure | Ave. Secretion IC$_{50}$ (μM) | Ave. Translocation IC$_{50}$ (μM)[1] | Ave. CC$_{50}$ (μM) | melting point (° C.) |
|---|---|---|---|---|---|
| 2083 | 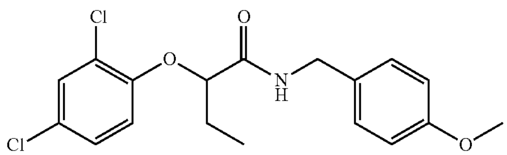 [SMILES: CCC(Oc1ccc(Cl)cc1Cl)C(=O)NCc1ccc(OC)cc1] | 8.1 | 29.3 | n.d. | 86 |
| 2087 | 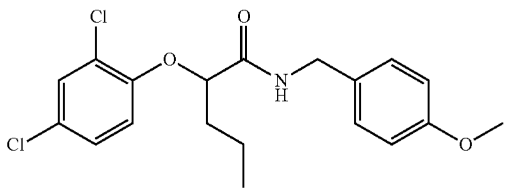 [SMILES: CCCC(Oc1ccc(Cl)cc1Cl)C(=O)NCc1ccc(OC)cc1] | 16% @50 μM | n.d. | n.d. | 103 |
| 2148 | 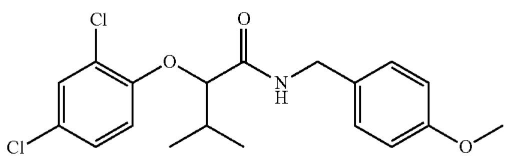 [SMILES: COc1ccc(CNC(=O)C(Oc2ccc(Cl)cc2Cl)C(C)C)cc1] | 210 | n.d. | n.d. | 77 |
| 1942 | 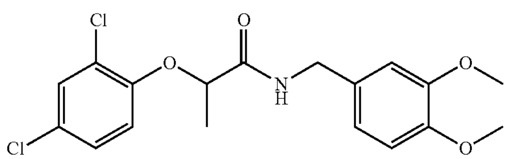 [SMILES: COc1ccc(CNC(=O)C(C)Oc2ccc(Cl)cc2Cl)cc1OC] | 22.2 | >100 | n.d. | 127 |
| 2082 | 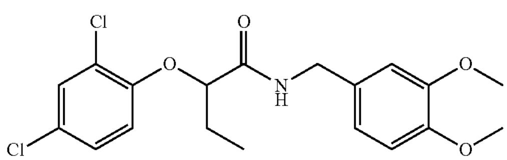 [SMILES: CCC(Oc1ccc(Cl)cc1Cl)C(=O)NCc1ccc(OC)c(OC)c1] | 16.3 | >100 | n.d. | 117 |
| 2086 | 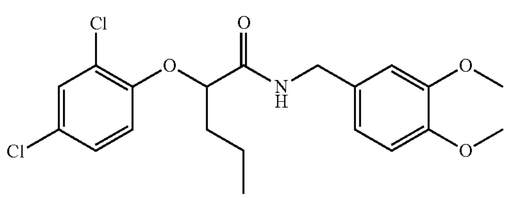 [SMILES: CCCC(Oc1ccc(Cl)cc1Cl)C(=O)NCc1ccc(OC)c(OC)c1] | 18% @50 μM | n.d. | n.d. | 82 |
| 2147 | 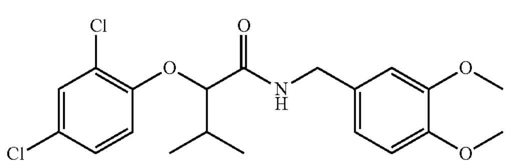 [SMILES: COc1ccc(CNC(=O)C(Oc2ccc(Cl)cc2Cl)C(C)C)cc1OC] | 94.9 | >100 | n.d. | 109 |
| 2159 | 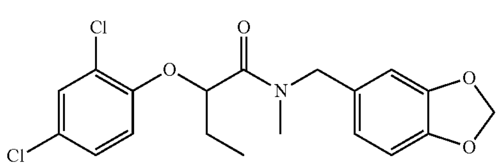 [SMILES: CCC(Oc1ccc(Cl)cc1Cl)C(=O)N(C)Cc1ccc2c(c1)OCO2] | 19.1 | >100 | n.d. | n.a. |

TABLE 4-continued

| MBX Cmpd. | Structure | Ave. Secretion IC$_{50}$ (μM) | Ave. Translocation IC$_{50}$ (μM)[1] | Ave. CC$_{50}$ (μM) | melting point (° C.) |
|---|---|---|---|---|---|
| 2359 | ![structure] | 1.5 | 5.2 | >100 | 126 | n.d. = not determined

[1] Compounds that have detectable activity in the T3SS secretion assay are also expected to have activity in the T3SS translocation assay, but no IC$_{50}$ value could be determined from the concentration range examined in those experiments with values indicated as >100 for the Ave. Translocation IC$_{50}$.

The results of these studies underscored the unexpected effect of alterations on the methyl acetamide scaffold. For example, whereas preparation of an α-ethyl analog of MBX-1641 (see MBX-2081) led to a 3-4-fold increase in potency as a T3SS inhibitor, elimination of the α-methyl in a des-methyl analog, and preparation of α-dimethyl, α-propyl and α-isopropyl analogs, led to significantly inferior performance in T3SS-mediated secretion (cf. MBX-2085, MBX-2146). Alteration of the linking moieties led to similarly divergent results: substitution of the amide had a negative impact on T3SS-mediated secretion inhibition (data not shown), whereas methyl substitution or dimethyl substitution at the linker bridging the amide group to the terminal aryl substituent led to IC$_{50}$ values that were 34% and 29% lower, respectively (data not shown). Similarly, alteration of the linking moiety to the α carbon led to divergent results: preparation of an analog having a thio bridge (—S—) instead of an oxa bridge (—O—) led to IC$_{50}$ values that were 29% lower, whereas preparation of analogs having divalent amino (—NH—) or sulfonyl bridges had an adverse effect on IC$_{50}$ values. (data not shown).

Figure 2:
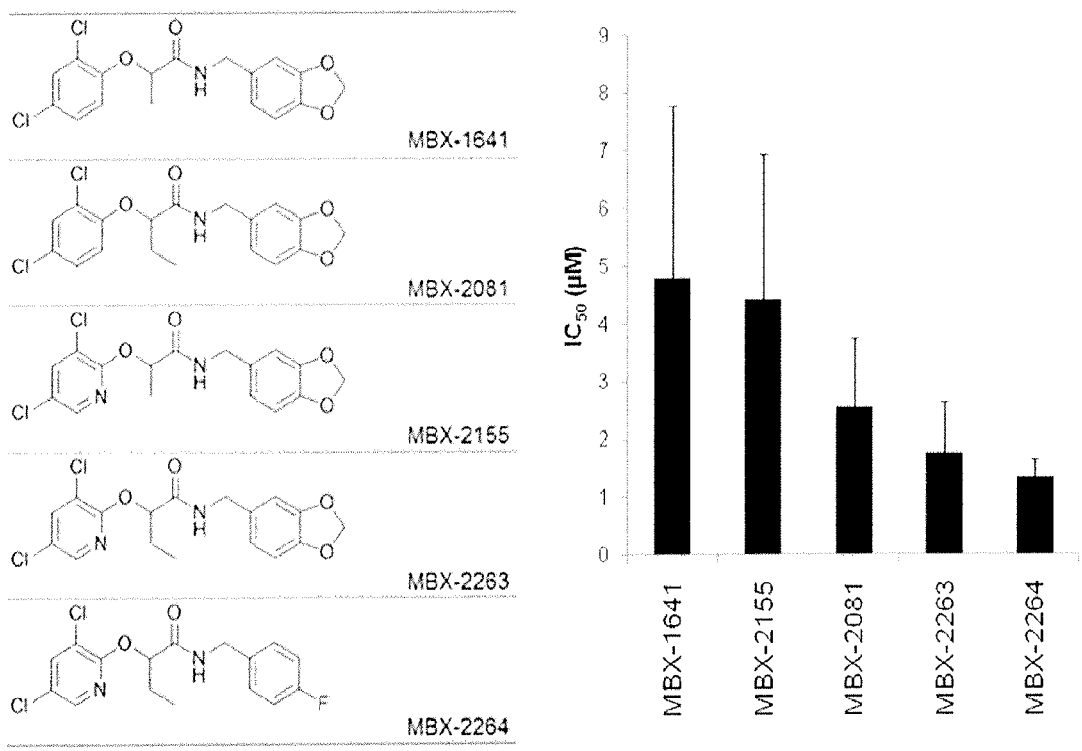
FIG. 2 is a bar graph showing the progression in properties of a series of analogs and indicates that certain beneficial structural alterations on an acetamide scaffold may have additive effects. The compounds all show improvements (i.e., decreases in $IC_{50}$ values in the ExoS'βLA assay) over a reference inhibitor, MBX-1641. Compounds MBX-2155, MBX-2081, MBX-2263, and MBX-2264 are compared, and the structures of the compounds appear to the left of the graph.

Although the effect of alterations on the scaffold structure was hard to predict, examination of data obtained on individually synthesized compounds indicated that the effects of structural alterations could be additive. For example, consideration of the series of compounds MBX-1641, MBX-2155, MBX-2081, MBX-2263, and MBX-2264 showed a progressive decrease in IC$_{50}$ value. See, FIG. 2.

Consideration of the foregoing data defined a new group of compounds of related structure that are useful as T3SS inhibitor compounds and have potency and/or toxicity profiles that make them candidates for use as therapeutic agents. The new family of inhibitor compounds can be described by the formula I:

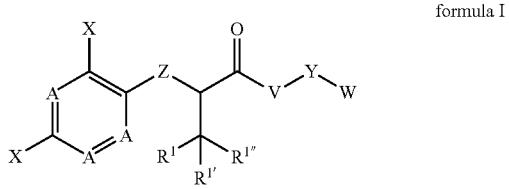

formula I wherein
A is independently CH or N;
X is independently selected from hydrogen or halogen;
Z is O, S, NH; or NR$^3$, wherein R$^3$ is alkyl;
R$^1$, R$^{1'}$, and R$^{1''}$ are selected independently from: hydrogen, halogen, alkyl, hydroxy, alkoxy, alkylthio, or cyano, wherein no more than two of the preceding radicals is hydrogen;

V is NR$^2$, O, or CR$^3$R$^4$;
R$^2$, R$^3$, and R$^4$ are independently hydrogen or alkyl;
Y is selected from:
a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy;
oxygen;
or NR$^5$ where R$^5$ is hydrogen or alkyl;
W is an aryl or heteroaryl radical forming a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy, and wherein any two substituents together may form an aromatic or non-aromatic ring structure fused with said aryl or heteroaryl radical W, which substituents found on W also may be optionally bonded covalently to either Y or R$^2$, or both Y and R$^2$, to form heterocyclic or carbocyclic ring systems, which ring systems may be aromatic, heteroaromatic, or partly aromatic (that is, one or more rings being aromatic and one or more rings being non-aromatic (saturated)).

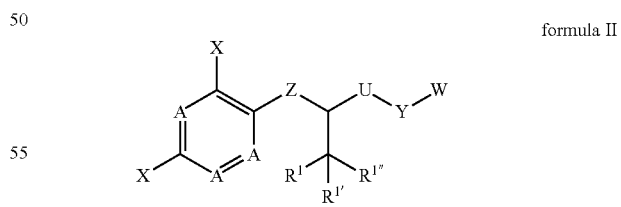

formula II wherein
A is independently CH or N;
X is independently selected from hydrogen or halogen;
Z is O, S, NH; or NR$^3$, where R$^3$ is alkyl;
R$^1$, R$^{1'}$, and R$^{1''}$ are selected independently from: hydrogen, halogen, alkyl, hydroxy, alkoxy, alkylthio, or cyano, wherein no more than two of the preceding radicals is hydrogen;
R$^2$, R$^3$, and R$^4$ are independently hydrogen or alkyl;

U is a divalent 5- or 6-membered heterocyclic ring selected from: oxazole, oxazoline, isoxazole, isoxazoline, 1,2,3 triazole, 1,2,4-triazole, 1,2,4-oxadiazole, 1,3,4-oxadiazole, 1,2-oxazine, 1,3-oxazine, pyrimidine, pyridazine, pyrazine, Y is selected from:

a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy;

oxygen;

or $NR^5$ where $R^5$ is hydrogen or alkyl;

W is an aryl or heteroaryl radical forming a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy, and wherein any two substituents together may form an aromatic or non-aromatic ring structure fused with said aryl or heteroaryl radical W, which substituents found on W also may be optionally bonded covalently to either Y or $R^2$, or both Y and $R^2$, to form heterocyclic or carbocyclic ring systems, which ring systems may be aromatic, heteroaromatic, or partly aromatic (that is, one or more rings being aromatic and one or more rings being non-aromatic (saturated)).

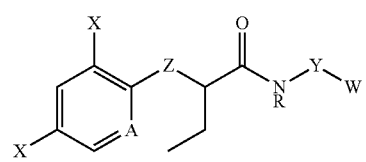

formula III wherein

A is CH or N;

X is independently selected from hydrogen or halogen;

R is hydrogen or methyl;

Y is a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy;

Z is O, S, or NH or $NR^3$; and

W is an aryl or heteroaryl radical forming a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, hydroxyl, amino, carboxamido, carboxyl, cyano, sulfonamido, sulfonyl, alkyl, alkenyl, alkynyl, cycloalkyl, heterocycloalkyl, aryl, heteroaryl, alkoxy, alkylthio, aryloxy, and heteroaryloxy, and wherein any two substituents together may form an aromatic or non-aromatic ring structure fused with said aryl or heteroaryl radical W, which substituents found on W also may be optionally bonded covalently to either Y or $R^2$, or both Y and $R^2$, to form heterocyclic or carbocyclic ring systems, which ring systems may be aromatic, heteroaromatic, or partly aromatic (that is, one or more rings being aromatic and one or more rings being non-aromatic (saturated)).

Additional syntheses were carried out to prepare conformationally constrained analogs in which the acetamide nitrogen is bound directly to a fused ring structure or is included in a multi-ring structure. Examples of conformationally constrained compounds are shown in Table 5.

TABLE 5

| MBX Cmpd. | Structure |
|---|---|
| 2188 | 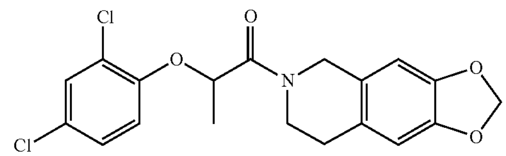 [SMILES: CC(Oc1ccc(Cl)cc1Cl)C(=O)N1CCc2cc3c(cc2C1)OCO3] |
| 2189 | 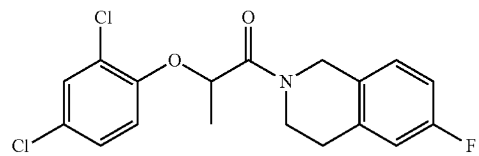 [SMILES: CC(Oc1ccc(Cl)cc1Cl)C(=O)N1CCc2cc(F)ccc2C1] |
| 2190 | 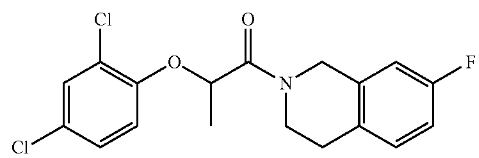 [SMILES: CC(Oc1ccc(Cl)cc1Cl)C(=O)N1CCc2ccc(F)cc2C1] |

These results led to the inclusion of additional structures in the family of formula I compounds, for example, compounds of the formulae IV and V:

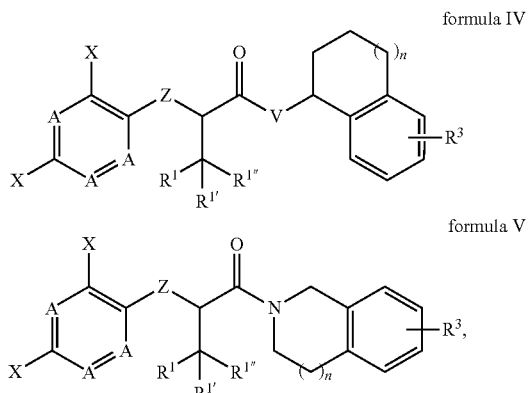

where the values for A, X, Z, $R^1$, $R^{1'}$, $R^{1''}$, and V are as defined above, and where n is 0 (denoting a five-member ring), 1, 2, or 3, and $R^3$ is selected from the group of hydrogen, halo, hydroxyl, amino, carboxamido, carboxyl, cyano, sulfonamido, sulfonyl, alkyl, alkenyl, alkynyl, cycloalkyl, heterocycloalkyl, aryl, heteroaryl, alkoxy, alkylthio, aryloxy, and heteroaryloxy.

Where alternative values for the "B" aryl moiety are included, the compounds of formulae IV and V may be depicted as follows:

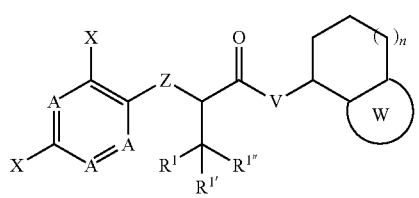

formula VI

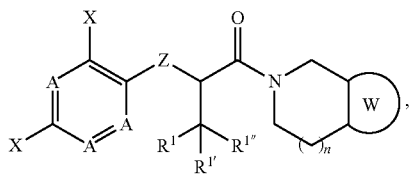

formula VII where the values for A, X, Z, $R^1$, $R^{1'}$, $R^{1''}$, and V, are as defined above for formula I, and where n is 0 (denoting a five-member ring), 1, 2, or 3, and where W is an aryl or heteroaryl radical forming a five-membered or six-membered ring fused with the carbocyclic ring bonded with the —NV— moiety in formula VI or fused with the nitrogen-containing heterocyclic ring moiety in formula VII and which may be additionally fused with from 1 to 3 aryl, heteroaryl, cycloalkyl, or heterocycloalkyl rings, which W radical may be unsubstituted or substituted with up to four substituents selected from halo, hydroxyl, amino, carboxamido, carboxyl, cyano, sulfonamido, sulfonyl, alkyl, alkenyl, alkynyl, cycloalkyl, heterocycloalkyl, aryl, heteroaryl, alkoxy, alkylthio, aryloxy, and heteroaryloxy.

Thus, to include conformationally constrained analogs in the discovered family of inhibitors, in formula I the values for Y will include structures wherein Y is a cyclic hydrocarbon ring having from 5-10 carbon atoms which is fused with the radical W; or, alternatively, Y and NV together form a heterocyclic ring having from 4-10 carbon atoms fused with the radical W.

Example 3

Determination of Active and Inactive Isomers

The compounds of formula I have an asymmetric center (α carbon), and therefore the synthesis of these compounds can yield a mixture of optical isomers (racemic mixture), or either R- or S-isomers, depending on the method used for synthesis. The initial synthesis of MBX-1641 provided a racemic mixture. To determine whether both isomers contribute to the inhibitory properties of such compounds, the separate isomers of compound MBX-1641 were synthesized by treating dichlorophenol with the commercially available (S)-ethyl lactate (to yield the optically pure R-isomer of MBX-1641) or with commercially available (R)-ethyl lactate (to yield the optically pure S-isomer of MBX-1641). Reaction of the hydroxy group of the (S)-ethyl lactate with dichlorophenol under Mitsunobu conditions proceeds with inversion of configuration at the chiral center to provide the (R)-ester. Saponification of the ester, followed by peptide coupling, provides compound MBX-1684 as a single enantiomer, which is the R-isomer of MBX 1641. Similarly, the other enantiomer (compound designated MBX-1686, which is the S-isomer of MBX 1641) is produced in the same way beginning from (R)-ethyl lactate.

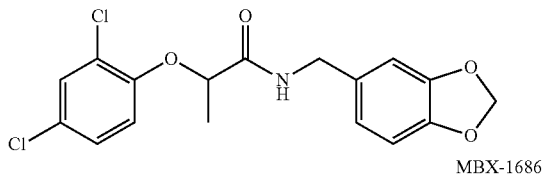

MBX-1641

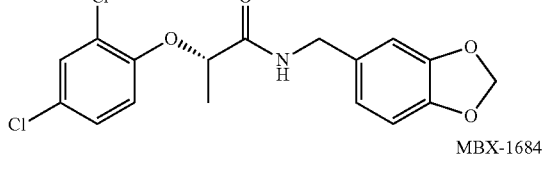

MBX-1686

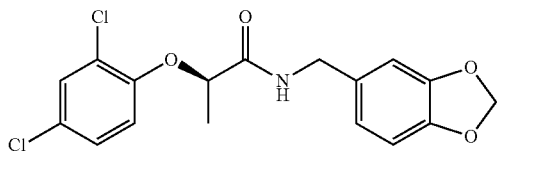

MBX-1684

The racemate and each of the enantiomers were tested for inhibition of T3 SS-mediated secretion of an effector toxin-β-lactamase fusion protein (ExoS'-βLA) using *P. aeruginosa* strain MDM973 (PAK/pUCP24GW-lacI$^Q$-lacPO-exoS::blaM, Table 1).

Figure 3:
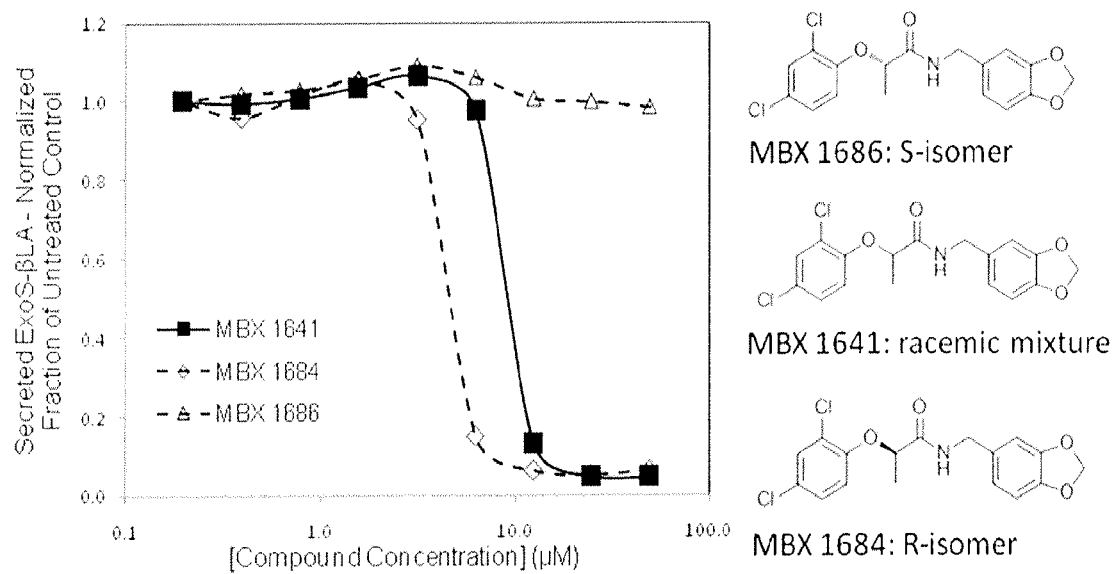
FIG. 3 is a graph showing the effects of compound MBX-1641 and its R- and S-enantiomers on ExoS'-βLA secretion from *P. aeruginosa*. Concentration-dependence for MBX-1641 and its two stereoisomers, MBX-1684 (R-enantiomer) and MBX-1686 (S-enantiomer) were determined by the rate of nitrocefin cleavage by secreted ExoS'-βLA and calculated as the fraction of cleavage in the absence of inhibitor. Inhibition of secretion by the racemic mixture MBX-1641 (■, solid line), R-enantiomer MBX-1684 (◇, dashed line), and S-enantiomer MBX-1686 (Δ, dashed line) are shown.

The results are shown in FIG. 3.

Figure 4:
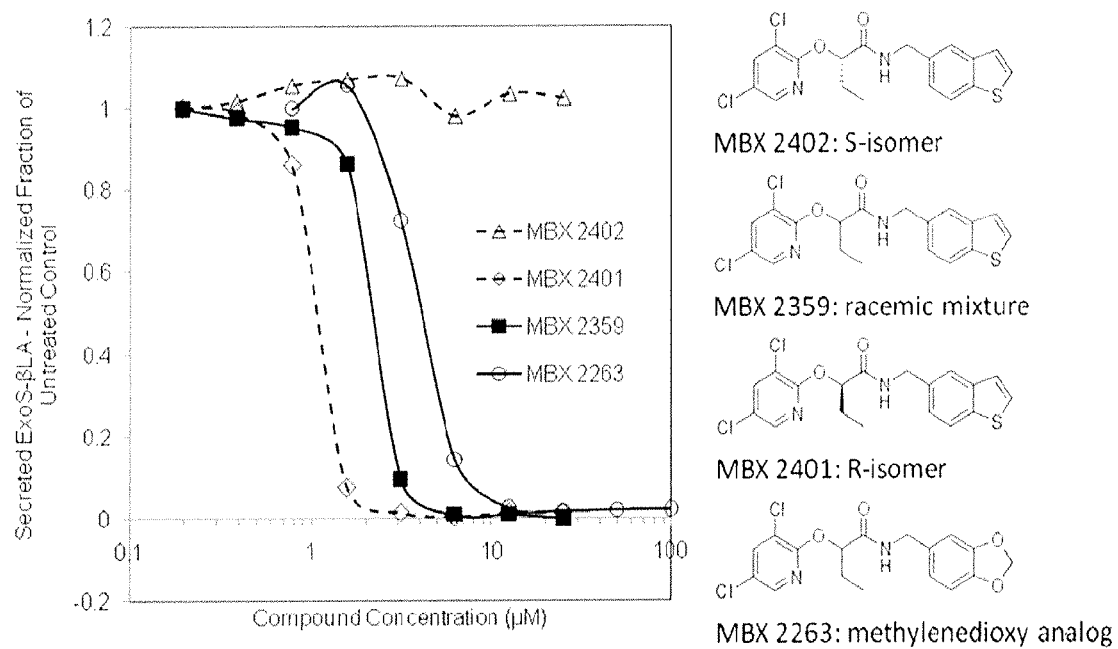
FIG. 4 is a graph showing the effects of α-ethyl compound MBX-2359 and its R- and S-enantiomers on ExoS'-βLA secretion from *P. aeruginosa*. Concentration-dependence for MBX-2359 and its two stereoisomers, MBX-2401 (R-enantiomer) and MBX-2402 (S-enantiomer) were determined by the rate of nitrocefin cleavage by secreted ExoS'-βLA and calculated as the fraction of cleavage in the absence of inhibitor. Inhibition of secretion by the racemic mixture MBX-2359 (■, solid line), R-enantiomer MBX-2401 (◇, dashed line), and S-enantiomer MBX-2402 (Δ, dashed line) are shown. Also shown are results for another α-ethyl-substituted compound, MBX-2263 (racemate, ○).

A similar comparison was performed using α-ethyl analogs according to this invention, to investigate isomer effects in that class of compounds. Referring to FIG. 4, the effects of α-ethyl compound MBX-2359 and its R- and S-enantiomers on ExoS'-βLA secretion from *P. aeruginosa* is shown.

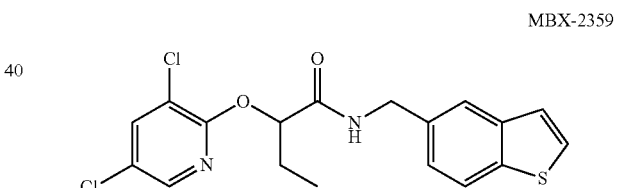

MBX-2359

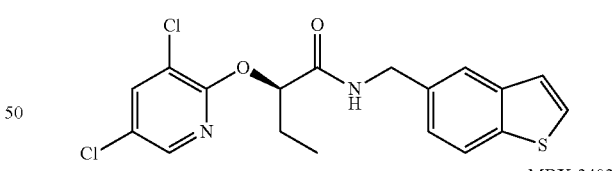

MBX-2401

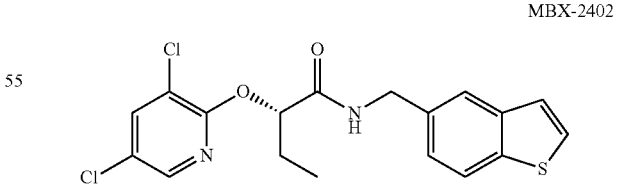

MBX-2402

Concentration-dependence for MBX-2359 and its two stereoisomers, MBX-2401 enantiomer) and MBX-2402 (S-enantiomer), plus an additional compound MBX-2263 was determined by the rate of nitrocefin cleavage by secreted ExoS'-βLA and calculated as the fraction of cleavage in the absence of inhibitor. As shown in FIG. 4, potent inhibition of secretion by the racemic mixture MBX-2359 (■), R-enantiomer MBX- 2401 (◇), and another α-ethyl analog, compound MBX-2263 (racemate, ○) is clearly shown, whereas the S-enantiomer MBX-2402 (Δ) shows little inhibitory effect.

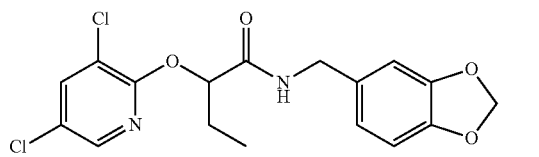

MBX-2263

It is evident that the T3SS inhibitory properties of the compounds of formula I reside primarily in the R-isomer, although the racemic mixture is also active. This is again consistent with the concept that the present compounds target a particular binding site.

All publications, patent applications, patents, and other documents cited herein are incorporated by reference in their entirety. In case of conflict, the present specification, including definitions, will control. In addition, the materials, methods, and examples are illustrative only and not intended to be Obvious variations to the disclosed compounds and alternative embodiments of the invention will be apparent to those skilled in the art in view of the foregoing disclosure. All such obvious variants and alternatives are considered to be within the scope of the invention as described herein.

The invention claimed is:

1. A bacterial type III secretion system (T3SS) inhibitor compound of formula I:

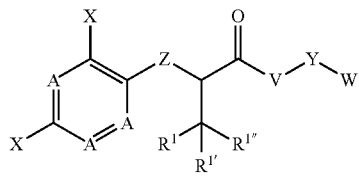

formula I wherein
each A is independently CH or N;
X is Cl;
Z is O or S
$R^1$, $R^{1''}$, and $R^{1'''}$ are selected independently from: hydrogen, halogen, or alkyl, wherein no more than two of the preceding radicals is hydrogen;
V is $NR^2$;
$R^2$ is independently hydrogen or alkyl;
Y is selected from:
a divalent straight-chain, branched, or cyclic alkyl, alkenyl or alkynyl radical of from 1 to 6 carbon atoms, which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio, aryloxy, and heteroaryloxy;
W is an aryl or heteroaryl radical comprising a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio, aryloxy, and heteroaryloxy, wherein W may not be unsubstituted phenyl and
wherein any two substituents together may form an aromatic or non-aromatic ring structure fused with said aryl or heteroaryl radical W, which substituents found on W also may be optionally bonded covalently to Y to form heterocyclic or carbocyclic ring systems.

2. A bacterial type III secretion system (T3SS) inhibitor compound of formula III:

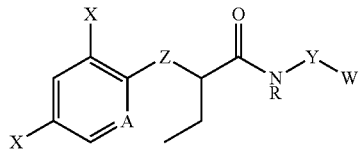

formula III wherein
A is CH or N;
X is Cl;
R is hydrogen or methyl;
Y is a divalent straight-chain, branched, or cyclic alkyl, alkenyl or alkynyl radical of from 1 to 6 carbon atoms, which may contain one or more heteroatoms, and which may be unsubstituted or substituted with up to four substituents selected from halo, cyano, hydroxy, amino, alkylamino, carboxyl, alkoxycarbonyl, carboxamido, acylamino, amidino, sulfonamido, aminosulfonyl, alkylsulfonyl, aryl, heteroaryl, alkoxy, alkylthio; aryloxy, and heteroaryloxy;
Z is O or S; and
W is an aryl or heteroaryl radical comprising a five-membered or six-membered ring which may be additionally fused with from 1 to 3 aryl, heteroaryl, cycloalkyl, or heterocycloalkyl rings, which W radical may be unsubstituted or substituted with up to four substituents selected from halo, hydroxyl, amino, carboxamido, carboxyl, cyano, sulfonamido, sulfonyl, alkyl, alkenyl, alkynyl, cycloalkyl, heterocycloalkyl, aryl, heteroaryl, alkoxy, alkylthio, aryloxy, and heteroaryloxy, wherein W may not be unsubstituted phenyl, and wherein any two substituents together may form an aromatic or non-aromatic ring structure fused with said aryl or heteroaryl radical W, which substituents found on W also may be optionally bonded covalently to Y to form heterocyclic or carbocyclic ring systems.

3. The T3SS inhibitor compound according to claim 2, wherein W is selected from

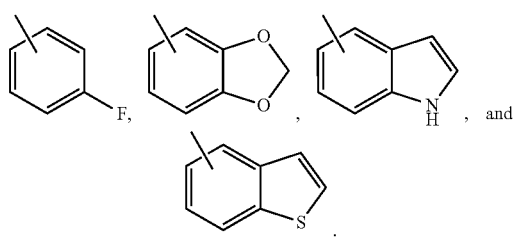
4. The compound according to claim 1 selected from the group consisting of:
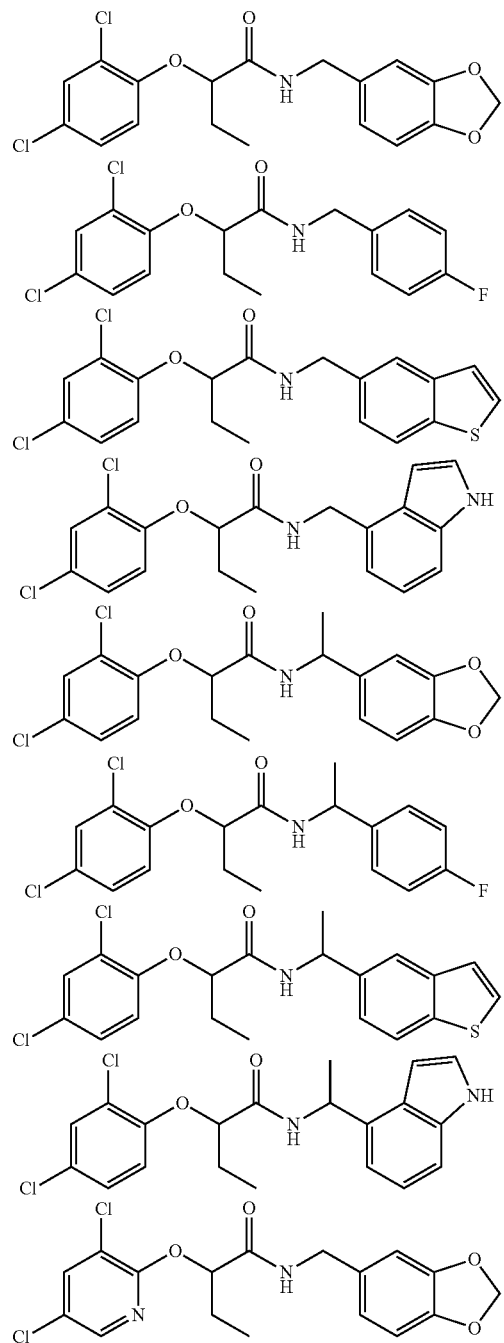
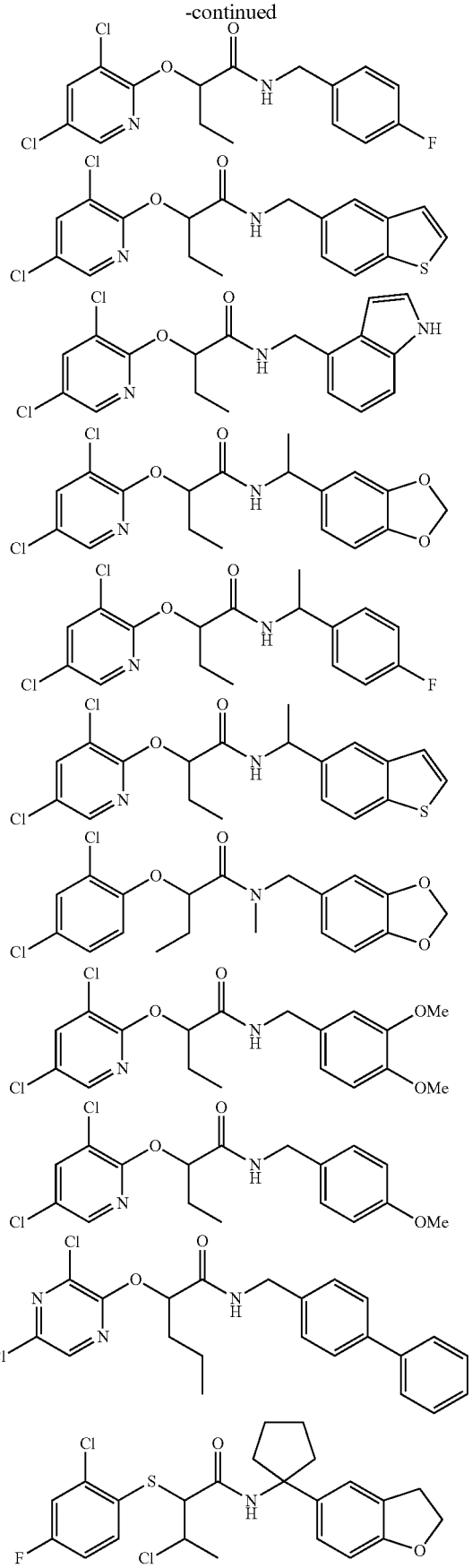

63
-continued
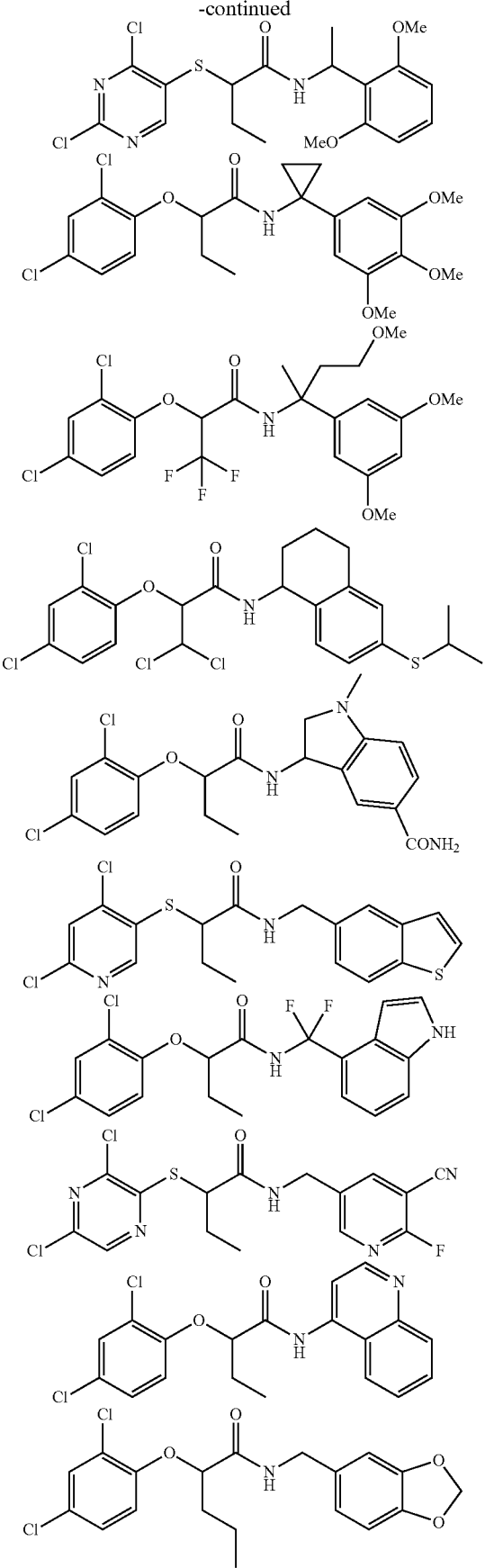
64
-continued
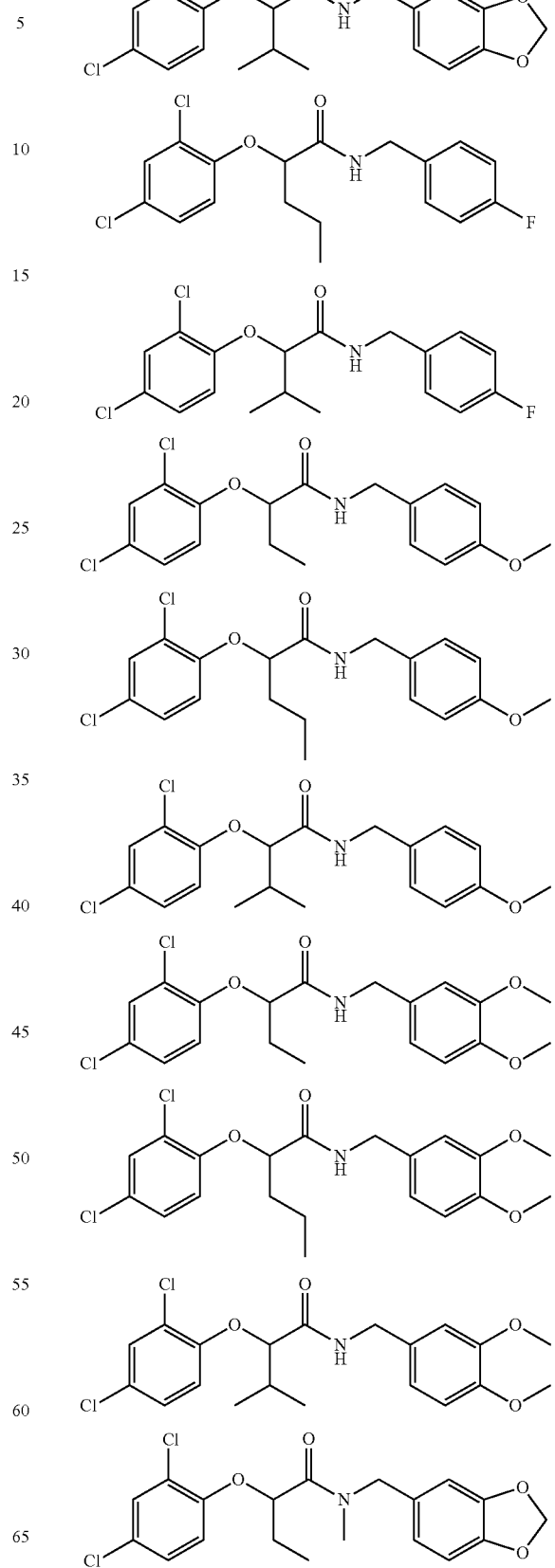

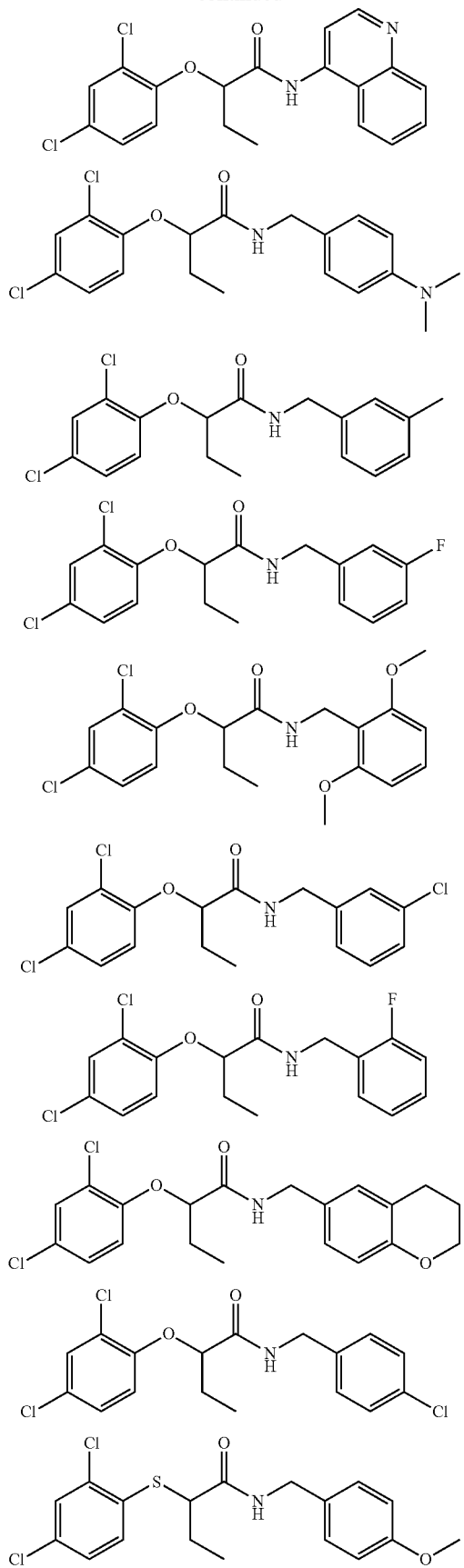
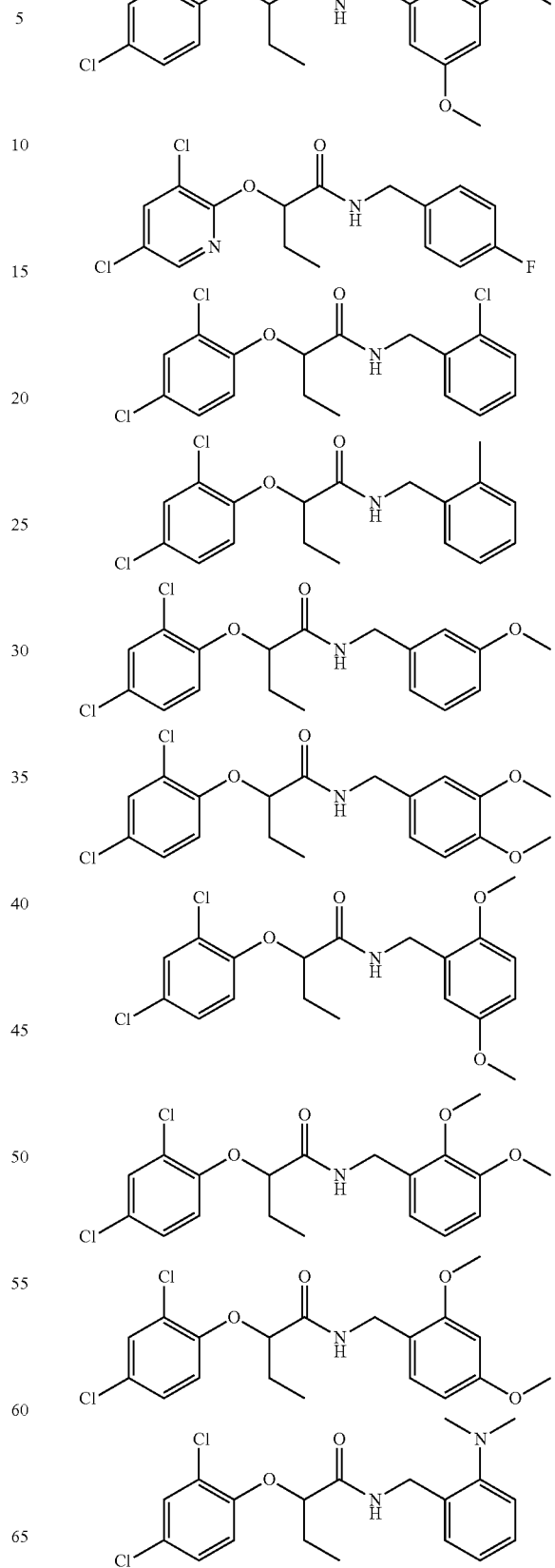

-continued
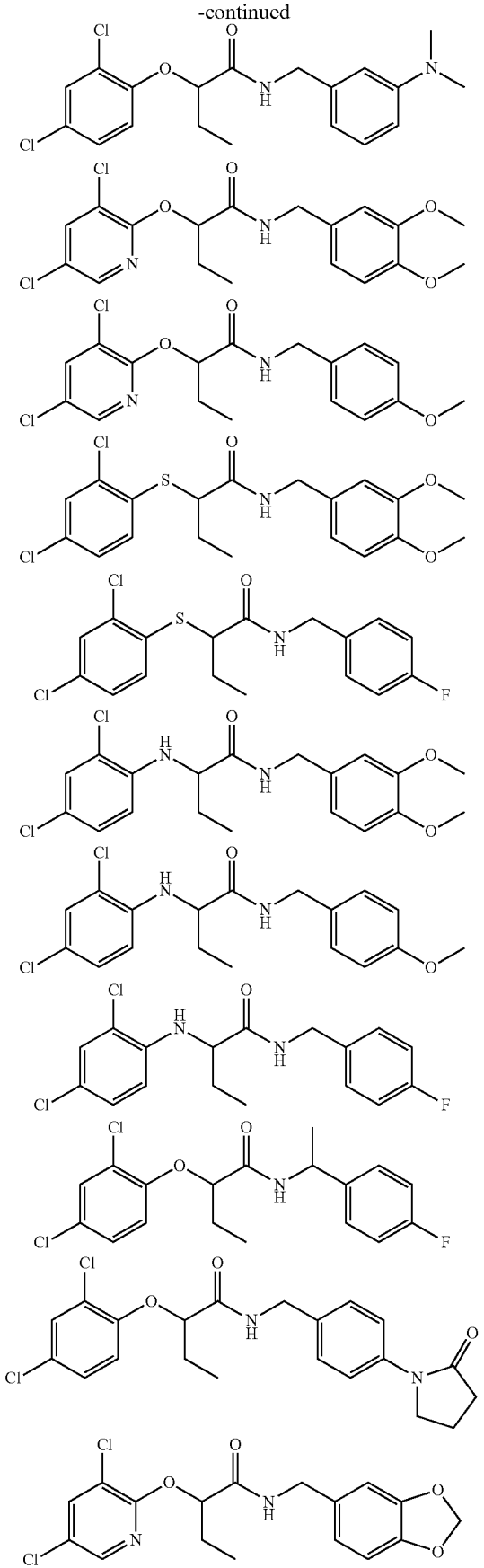
-continued
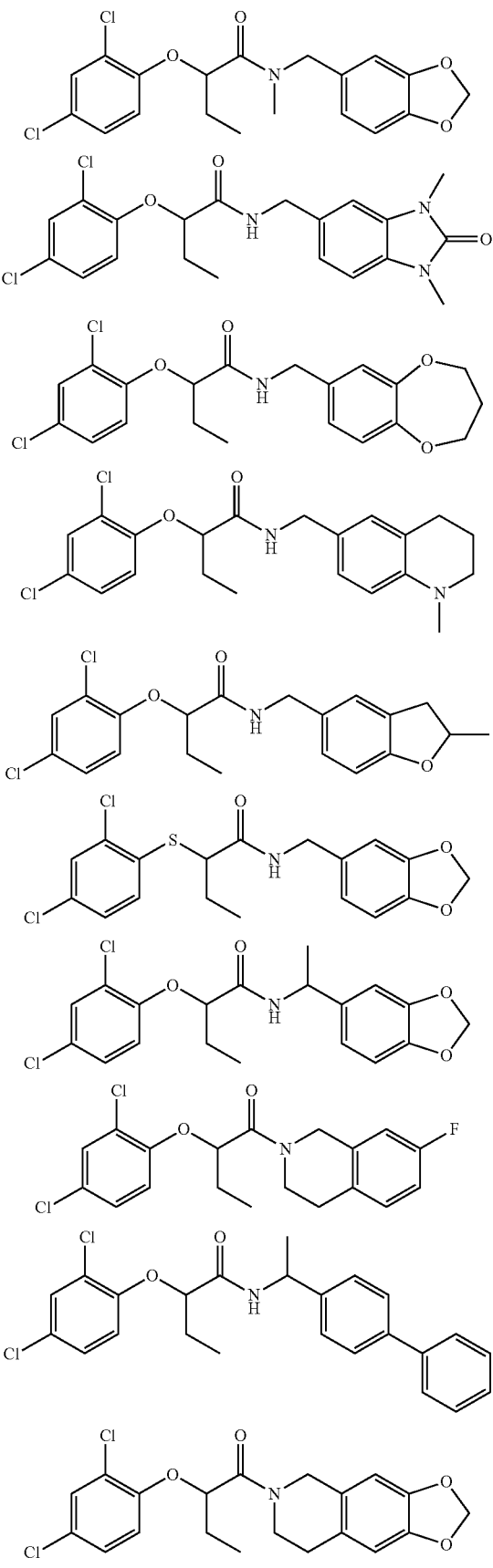

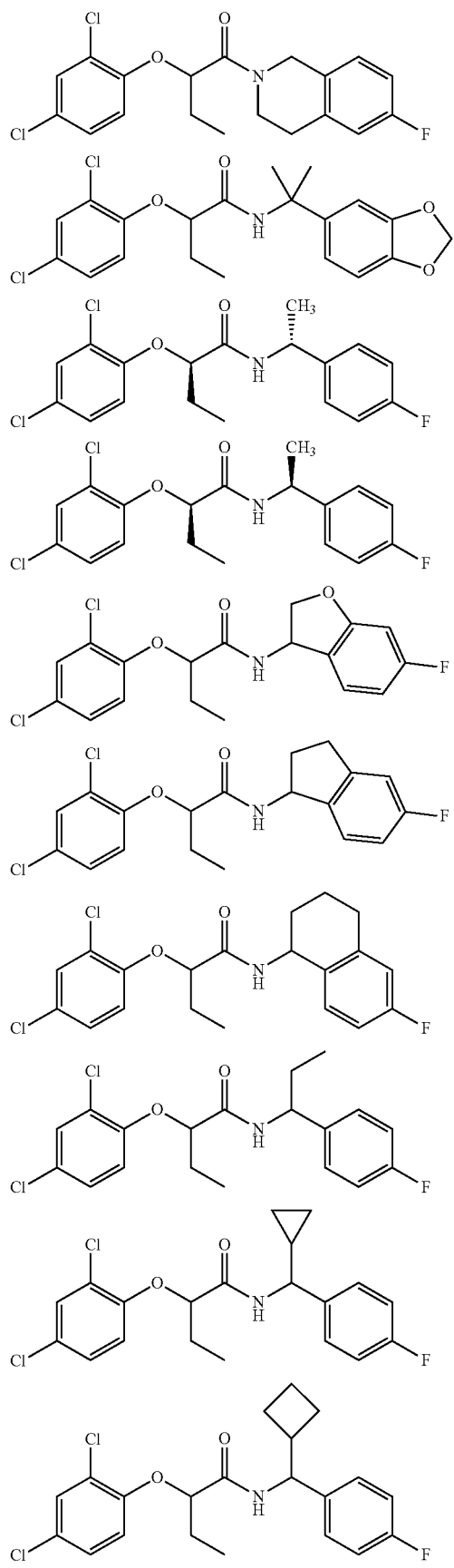
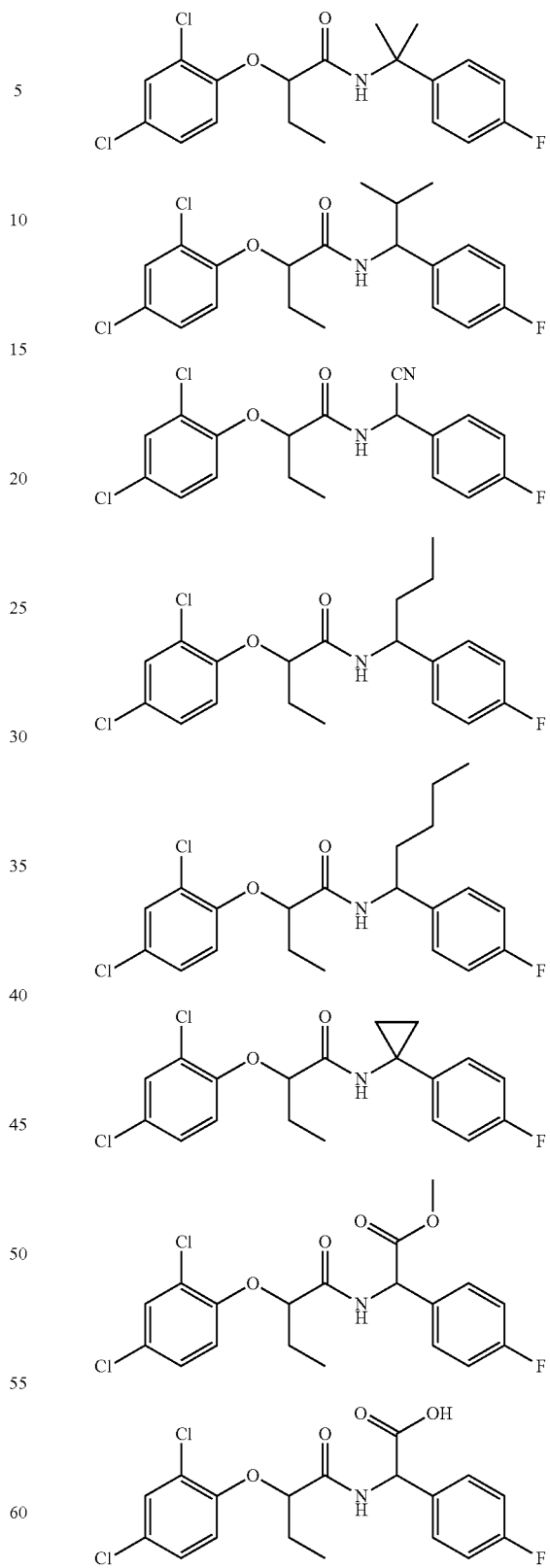
and particular isomers of any of the foregoing compounds.
5. The compound according to claim 1, comprising the R-isomer in substantially pure form.

6. The compound according to claim 4, selected from

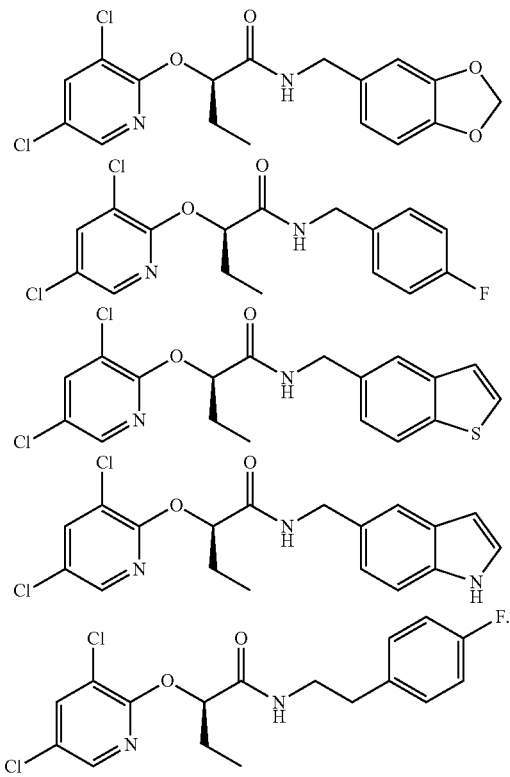

7. A pharmaceutical composition comprising one or more bacterial T3SS inhibitor compounds according to claim 1 and a pharmaceutically acceptable carrier or excipient.

8. The pharmaceutical composition according to claim 7, wherein said one or more T3SS inhibitor compounds is the R-isomer in substantially pure form.

9. A method for treating an individual infected with or exposed to a Gram-negative bacterium comprising administering to said individual an effective amount to inhibit T3SS-mediated effector secretion of a compound according to claim 1.

10. The method according to claim 9, wherein said individual is human.

11. The method according to claim 9, wherein said Gram-negative bacterium is of the genus *Pseudomonas, Salmonella, Yersinia*, or *Chlamydia*.

12. The method according to claim 9, wherein said Gram-negative bacterium is *Pseudomonas aeruginosa, Yersinia pestis* or *Chlamydia trachomatis*.

13. The method according to claim 9, wherein said Gram-negative bacterium is *Pseudomonas aeruginosa*.

14. The method according to claim 9, further comprising administering an additional active ingredient selected from the group consisting of an antibiotic, an antibody, an antiviral agent, an anticancer agent, an analgesic, an immunostimulatory agent, a natural, synthetic or semisynthetic hormone, a central nervous system stimulant, an antiemetic agent, an anti-histamine, an erythropoietin, a complement stimulating agent, a sedative, a muscle relaxant agent, an anesthetic agent, an anticonvulsive agent, an antidepressant, an antipsychotic agent, and combinations thereof.

* * * * *